US012768843B2

(12) United States Patent
Wakeland et al.

(10) Patent No.: US 12,768,843 B2
(45) Date of Patent: Oct. 20, 2026

(54) PREDICTION AND TREATMENT OF IMMUNOTHERAPEUTIC TOXICITY

(71) Applicant: The Board of Regents of the University of Texas System, Austin, TX (US)

(72) Inventors: Edward Wakeland, Dallas, TX (US); David E. Gerber, Dallas, TX (US); Quan Li, Dallas, TX (US); Shaheen Khan, Dallas, TX (US); Saad Khan, Dallas, TX (US); Yang Xie, Dallas, TX (US); Jason Y. Park, Dallas, TX (US); Farjana Fattah, Dallas, TX (US); Xin Luo, Dallas, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 771 days.

(21) Appl. No.: 17/045,482

(22) PCT Filed: Apr. 8, 2019

(86) PCT No.: PCT/US2019/026275

§ 371 (c)(1),
(2) Date: Oct. 5, 2020

(87) PCT Pub. No.: WO2019/195823

PCT Pub. Date: Oct. 10, 2019

(65) Prior Publication Data

US 2021/0263045 A1 Aug. 26, 2021

Related U.S. Application Data

(60) Provisional application No. 62/654,025, filed on Apr. 6, 2018.

(51) Int. Cl.

| | |
|---|---|
| ***G01N 33/53*** | (2006.01) |
| ***A61K 39/395*** | (2006.01) |
| ***C07K 16/28*** | (2006.01) |
| ***G01N 33/564*** | (2006.01) |
| ***G01N 33/68*** | (2006.01) |
| *A61K 39/00* | (2006.01) |

(52) U.S. Cl.

CPC ..... *G01N 33/6863* (2013.01); *C07K 16/2818* (2013.01); *C07K 16/2827* (2013.01); *G01N 33/564* (2013.01); *G01N 33/68* (2013.01); *A61K 2039/505* (2013.01); *A61K 2039/507* (2013.01); *G01N 2333/521* (2013.01); *G01N 2333/535* (2013.01); *G01N 2800/52* (2013.01)

(58) Field of Classification Search

CPC ......... G01N 33/6863; G01N 2333/521; G01N 2800/52; G01N 2333/52

See application file for complete search history.

(56) References Cited

U.S. PATENT DOCUMENTS

| | | | | |
|---|---|---|---|---|
| 11,359,017 | B2 | 6/2022 | Fujimura | |
| 2015/0044224 | A1 | 2/2015 | Soliman et al. | |
| 2015/0110779 | A1 | 4/2015 | Shahabi et al. | |
| 2015/0118244 | A1 | 4/2015 | Shahabi et al. | |
| 2017/0298440 | A1 | 10/2017 | Fong et al. | |
| 2018/0128817 | A1 | 5/2018 | Weber et al. | |
| 2019/0336504 | A1* | 11/2019 | Gill | A61K 39/39558 |
| 2020/0038442 | A1 | 2/2020 | Rossi et al. | |
| 2020/0129566 | A1* | 4/2020 | Carbonnel | C12Q 1/6886 |
| 2020/0190585 | A1 | 6/2020 | Wassmann | |
| 2020/0284803 | A1 | 9/2020 | Gerber et al. | |
| 2021/0071258 | A1 | 3/2021 | DuBose et al. | |
| 2021/0231663 | A1 | 7/2021 | Budde et al. | |
| 2022/0225597 | A1* | 7/2022 | Chadwick | G01N 33/5088 |
| 2023/0296610 | A1 | 9/2023 | Adhikary et al. | |

FOREIGN PATENT DOCUMENTS

| | | | | |
|---|---|---|---|---|
| WO | 2012069462 | A1 | 5/2012 | |
| WO | 2014064240 | A1 | 5/2014 | |
| WO | 2017040464 | A1 | 3/2017 | |
| WO | 2018156448 | A1 | 8/2018 | |
| WO | WO 2018/183839 | * | 10/2018 | A61K 39/395 |

OTHER PUBLICATIONS

Kawashima et al, J Clin Pathol 58:1057-1063, 2005.*

International Patent Application No. PCT/US2019/026275 "International Search Report and Written Opinion" mailed Aug. 15, 2019, 13 pages.

Duarte et al. "Autoantibodies May Predict Immune-Related Toxicity: Results from a Phase I Study of Intralesional Bacillus Calmette-Guérin followed by Ipilimumab in Patients with Advanced Metastatic Melanoma," Frontiers in Immunology, Mar. 2, 2018 (Mar. 2, 2018), vol. 9, Issue 411, pp. 1-9.

Marin-Acevedo et al. "Cancer immunotherapy beyond immune checkpoint inhibitors," Journal of Herntaology & Oncology, Jan. 12, 2018 (Jan. 12, 2018), vol. 11, No. 8, pp. 1-25.

Chaput et al. "Baseline gut microbiota predicts clinical response and colitis in metastatic melanoma patients treated with ipilimumab", Annals of Oncology 28, Mar. 27, 2017, pp. 1368-1379. (12 pages).

Supplemental Data to: Chaput et al. "Baseline gut microbiota predicts clinical response and colitis in metastatic melanoma patients treated with ipilimumab", Annals of Oncology 28, Mar. 27, 2017, pp. 1368-1379. (8 pages).

Baum, "UTSW Medical Center Autoantigen Array," public on Dec. 25, 2014, located at https://www.ncbi.nlm.nih.gov/geo/query/acc.cgi?acc=GPLI 9451, retrieved from internet Apr. 16, 2018.

Champiat et al., "Management of immune checkpoint blockade dysimmune toxicities: a collaborative position paper," Annals of Oncology, 27:559-574, 2016.

(Continued)

*Primary Examiner* — Mark Halvorson

(74) *Attorney, Agent, or Firm* — NORTON ROSE FULBRIGHT US LLP

(57) ABSTRACT

The present disclosure is directed to methods and compositions for the prediction and treatment of immunotherapy-induced toxicities, as well as improved methods for the treatment of cancer with immunotherapies.

15 Claims, 17 Drawing Sheets

(56) References Cited

OTHER PUBLICATIONS

Donia et al., "Cancer immunotherapy in patients with preexisting autoimmune disorders," Semin Immunopathol., 39(3):333-337, 2017.
Gelao et al., "Immune checkpoint blockade in cancer treatment: a double-edged sword cross-targeting the host as an 'innocent bystander,'" Toxins, 6:914-933, 2014.
Howell et al., "Optimal management of immune-related toxicities associated with checkpoint inhibitors in lung cancer," Lung Cancer, 88(2):117-123, 2015.
Khan et al., "Characteristics and Mortality of Patients with Lung Cancer and Autoimmune Disease," Presentation Eastern Cooperative Oncology Group (ECOG) Young Investigator Symposium, Nov. 2016.
Khan et al., "Immune dysregulation in cancer patients developing immune-related adverse events," Brit J Cancer, 120(1):63-68, 2019.
Khan et al., "Prevalence of autoimmune conditions among patients with lung cancer: Implications for immunotherapy treatment options," Annual Meeting of the American Society of Clinical Oncology, J Clin Oneal., 34:suppl abstract 9039, 2016.
Khan et al., "Prevalence of Autoimmune Disease Among Patients With Lung Cancer: Implications for Immunotherapy Treatment Options," JAMA Oneal., 2(11):1507-1508, 2016.
Li et al., "Protein array autoantibody profiles for insights into systemic lupus erythematosus and incomplete lupus syndromes," Clinical and Experimental Immunology, 147:60-70, 2006.
Li et al., "Risk factors for ANA positivity in healthy persons," Arthritis Research & Therapy, 13:R38, 2011.
Manson et al., "Biomarkers associated with checkpoint inhibitors," Annals of Oncology, 27:1199-1206,2016.
Michot et al., "Immune-related adverse events with immune checkpoint blockade: a comprehensive review," European Journal of Cancer, 54:139-148, 2016.
PCT International Search Report and Written Opinion issued in International Application No. PCT/US2018/018594, mailed Jun. 29, 2018.
Postow et al., "Nivolumab and ipilimumab versus ipilimumab in untreated melanoma," N Engl J Med, 372(21):2006-2017, 2015.
Raj et al., "Regulatory polymorphisms modulate the expression of HLA class II molecules and promote autoimmunity," eLife, 5:e12089, 2016.
Topalian et al., "Safety, activity, and immune correlates of anti-PD-1 antibody in cancer," N Engl J Med, 366(26):2443-2454, 2012.
Wandstrat et al., "Autoantibody profiling to identify individuals at risk for systemic lupus erythematosus," Journal of Autoimmunity, 27: 153-160, 2006.
Kahler et al.Treatment and side effect management of CTLA-4 antibody therapy in metastatic melanoma.JDDG; 2011 • 9:277-285 (Year: 2011).
Day et al. Immune-Related Adverse Events Associated with Immune Checkpoint Inhibitors. Bio-Drugs (2016) 30:571-584 (Year:2016).
Fadel et al. Anti-CTLA4 Antibody-Induced Lupus Nephritis.(New England Journal Medicine 361; 2 Jul. 9, 2009 (Year: 2009).
Zhu et al.Autoantigen Microarray for High-throughput Autoantibody Profiling in Systemic Lupus ErythematosusGenomics Proteomics Bioinformatics 13 (2015) 210-218 (Year: 2015).
Olsen et al. Autoantibody profiling to follow evolution of lupus syndromes. (Arthritis Research & Therapy 2012, 14:R 174) (Year:2012).
Seret et al.Mesangial Cell-Specific Antibodies Are Central to the Pathogenesis of Lupus Nephritis.Clinical and Developmental Immunology vol. 2012, Article ID 579670, 8 pages. 2012 (Year: 2012).
Leslie, D. et al. "Autoantibodies as predictors of disease," The Journal of Clinical Investigation—Autoimmune diseases, Perspective Series, Nov. 2001, pp. 1417-1422, vol. 108, No. 10, DOI:10.1172/JCI200114452.
Quest Diagonostics, "Tests for Autoimmune Diseases," retrieved from the Internet Dec. 12, 2022 at <https://NWW.questdiagnostics.com/healthcare-professionals/clinical-education-center/faq/faq 177>, 8 pages.
Gonugunta AS, et al. Humoral and cellular correlates of a novel immune-related adverse event and its treatment. J Immunother Cancer. 2021;9(12).
Maecker HT, et al. Standardizing immunophenotyping for the Human Immunology Project. Nat Rev Immunol. 2012;12(3):191-200.
Subudhi SK, et al. Clonal expansion of CD8 T cells in the systemic circulation precedes development of ipilimumab-induced toxicities. Proc Natl Acad Sci U S A. Oct. 18, 2016;113(42):11919-11924. doi: 10.1073/pnas.1611421113. Epub Oct. 3, 2016. PMID: 27698113; PMCID: PMC5081579.
Jing Y, et al. Multi-omics prediction of immune-related adverse events during checkpoint immunotherapy. Nat Commun. Oct. 2, 2020;11(1):4946. doi: 10.1038/s41467-020-18742-9. PMID: 33009409; PMCID: PMC7532211.
Reschke R, et al. Distinct Immune Signatures Indicative of Treatment Response and Immune-Related Adverse Events in Melanoma Patients under Immune Checkpoint Inhibitor Therapy. Int J Mol Sci. Jul. 27, 2021;22(15):8017. doi: 10.3390/ijms22158017. PMID: 34360781; PMCID: PMC8348898.
Schilling HL, et al. Development of a Flow Cytometry Assay to Predict Immune Checkpoint Blockade-Related Complications. Front Immunol. Nov. 16, 2021;12:765644. doi: 10.3389/fimmu.2021.765644. PMID: 34868015; PMCID: PMC8637156.
Lozano AX, et al. T cell characteristics associated with toxicity to immune checkpoint blockade in patients with melanoma. Nat Med. Feb. 2022;28(2):353-362. doi: 10.1038/s41591-021-01623-z. Epub Jan. 13, 2022. PMID: 35027754; PMCID: PMC8866214.
Zhao C, et al. Contrasting autoimmune and treatment effects reveals baseline set points of immune toxicity following checkpoint inhibitor treatment. https://www.biorxiv.org/content/10.1101/2022.06.05.494592v1.full.
Franken A, et al. Single-cell transcriptomics identifies pathogenic T-helper 17.1 cells and pro-inflammatory monocytes in immune checkpoint inhibitor-related pneumonitis. J Immunother Cancer. Sep. 2022;10(9):e005323. doi: 10.1136/jitc-2022-005323. PMID: 36171010.
Das, R., et al. "Early B cell changes predict autoimmunity following combination immune checkpoint blockade." The Journal of clinical investigation 128.2 (2018): 715-720.
Gonugunta, A., et al. "Humoral and cellular correlates of a novel immune-related adverse event and its treatment." Journal for immunotherapy of cancer 9.12 (2021): e003585.
Von Itzstein, M., et al. "Immunotherapy use in patients with lung cancer and comorbidities." The Cancer Journal 26.6 (2020): 525-536.

* cited by examiner

| Cytokine/Chemokine | Baseline median | Post-Immunotherapy median (2-weeks) | P-value |
|---|---|---|---|
| CXCL9 | 244.3 | 604.5 | 0.002 |
| CXCL10 | 34.94 | 67.7 | <0.0001 |
| CXCL11 | 126.2 | 221.3 | 0.0472 |
| CXCL13 | 16.4 | 31.8 | 0.001 |

| Cytokine/Chemokine | Baseline median | Post-Immunotherapy median (6-weeks) | P-value |
|---|---|---|---|
| CXCL9 | 244.3 | 671.7 | 0.0002 |
| CXCL10 | 34.94 | 59.41 | 0.002 |
| CXCL11 | 126.2 | 184.1 | 0.04 |
| CXCL13 | 16.4 | 24.98 | 0.01 |
| CCL26 | 5.6 | 8.12 | 0.004 |
| IL-10 | 11.7 | 19.4 | 0.03 |

FIGS. 1A-E

| Cytokine/Chemokine | Baseline median | Post-Immunotherapy median (2-weeks) | P-value |
|---|---|---|---|
| CXCL9 | 344.3 | 604.5 | 0.002 |
| CXCL10 | 34.04 | 87.7 | <0.0001 |
| CXCL11 | 129.2 | 321.3 | 0.0470 |
| CXCL13 | 18.4 | 31.6 | 0.001 |

| Cytokine/Chemokine | Baseline median | Post-Immunotherapy median (6-weeks) | P-value |
|---|---|---|---|
| CXCL9 | 244.3 | 671.7 | 0.0002 |
| CXCL10 | 34.94 | 58.41 | 0.002 |
| CXCL11 | 129.2 | 184.1 | 0.04 |
| CXCL13 | 18.4 | 24.99 | 0.01 |
| CCL26 | 3.6 | 8.12 | 0.004 |
| IL-10 | 11.7 | 19.4 | 0.03 |

FIGS. 2A-E

1. Logistic regression test identify CXCL8, MIF35, CXCL16 and CCL23 as important predictors.

| | Estimate | Std. Error | z value | Pr(>\|z\|) | |
|---|---|---|---|---|---|
| (Intercept) | -5.07417 | 23.76236 | -0.214 | 0.8309 | |
| CCL21 | -1.01484 | 2.29803 | -0.442 | 0.6588 | |
| CCL27 | 2.76628 | 1.81903 | 1.521 | 0.1283 | |
| CCL11 | 0.01702 | 0.92656 | 0.018 | 0.9853 | |
| CX3CL1 | -0.60836 | 0.91837 | -0.662 | 0.5077 | |
| CXCL1 | 3.65089 | 4.75373 | 0.768 | 0.4425 | |
| CXCL8 | -2.04745 | 1.20178 | -1.704 | 0.0884 | |
| IL16 | 3.66932 | 2.24187 | 1.637 | 0.1017 | |
| CXCL10 | -1.40173 | 1.42407 | -0.984 | 0.3250 | |
| CXCL11 | 0.61914 | 0.70430 | 0.879 | 0.3794 | |
| CCL2 | 0.82494 | 1.17640 | 0.701 | 0.4832 | |
| CCL13 | -1.10047 | 1.98684 | -0.554 | 0.5797 | |
| CCL22 | 1.12191 | 0.84247 | 1.332 | 0.1830 | |
| MIF35 | 1.05991 | 0.47016 | 2.254 | 0.0242 | * |
| CXCL9 | 0.03049 | 1.05556 | 0.029 | 0.9770 | |
| CCL15 | -1.44615 | 1.13621 | -1.273 | 0.2031 | |
| CCL20 | -0.16036 | 0.63028 | -0.254 | 0.7992 | |
| CCL19 | -1.38370 | 1.11070 | -1.246 | 0.2128 | |
| CCL23 | 2.51892 | 1.16864 | 2.155 | 0.0311 | * |
| CXCL16 | -4.25080 | 1.89416 | -2.244 | 0.0248 | * |
| CXCL12 | -0.23550 | 1.16452 | -0.202 | 0.8397 | |
| CCL25 | -3.70941 | 2.62924 | -1.411 | 0.1583 | |

FIG. 4

```
Call:
glm(formula = AE ~ CXCL8 + CXCL16 + MIF35 + CCL23, family = binomial(link = "logit")
    data = training)

Deviance Residuals:
    Min       1Q   Median       3Q      Max
-1.4619  -0.9591  -0.6475   1.0643   1.7146

Coefficients:
             Estimate Std. Error z value Pr(>|z|)
(Intercept)    5.3037     5.8374   0.909   0.3636
CXCL8         -0.8224     0.4638  -1.773   0.0762
CXCL16        -0.8885     0.8502  -1.045   0.2960
MIF35          0.1331     0.1716   0.776   0.4379
CCL23          0.4419     0.4952   0.892   0.3722
```

Sensitivity: 0.92
Specificity: 0.6
Positive Predictive Value: 0.86
Negative Predictive Value 0.75

| IgG | pvalue |
|---|---|
| Fibrinogen.S | 0.00116976 |
| Entaktin.EDTA | 0.031566189 |
| complement.C7 | 0.04064084 |

| IgG | pvalue | t |
|---|---|---|
| Matrigel | 0.016736 | 2.494565 |
| Thyroglobulin | 0.035633 | 2.203519 |

| Control | No | Yes |
|---|---|---|
| 10 | 28 | 15 |

| IgG | pvalue | t |
|---|---|---|
| TPO | 0.030256 | 2.28902 |
| Chromatin | 0.046709 | 2.09131 |
| Thyroglobulin | 0.047621 | 2.28564 |

| No | Yes |
|---|---|
| 20 | 9 |

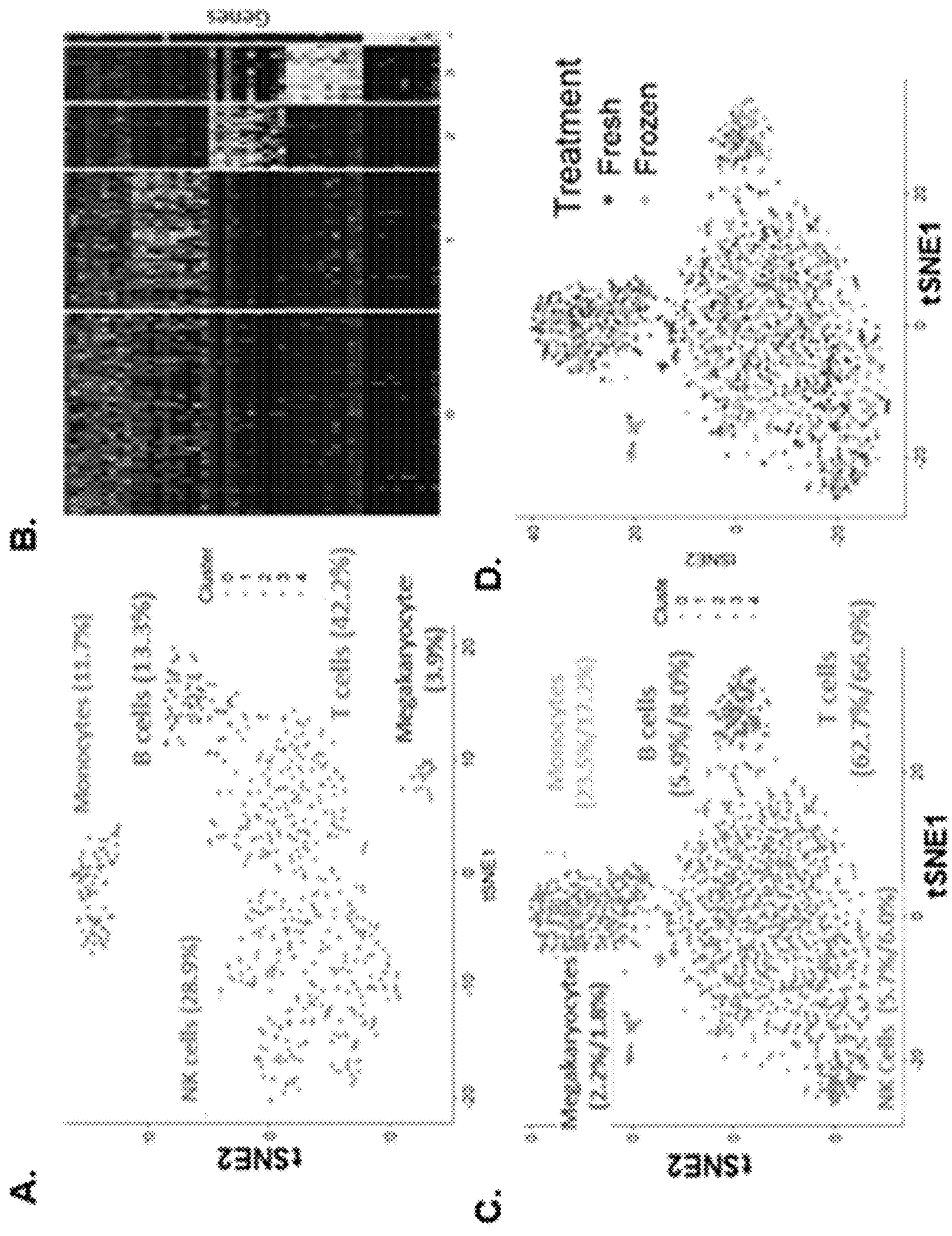
FIGS. 14A-D

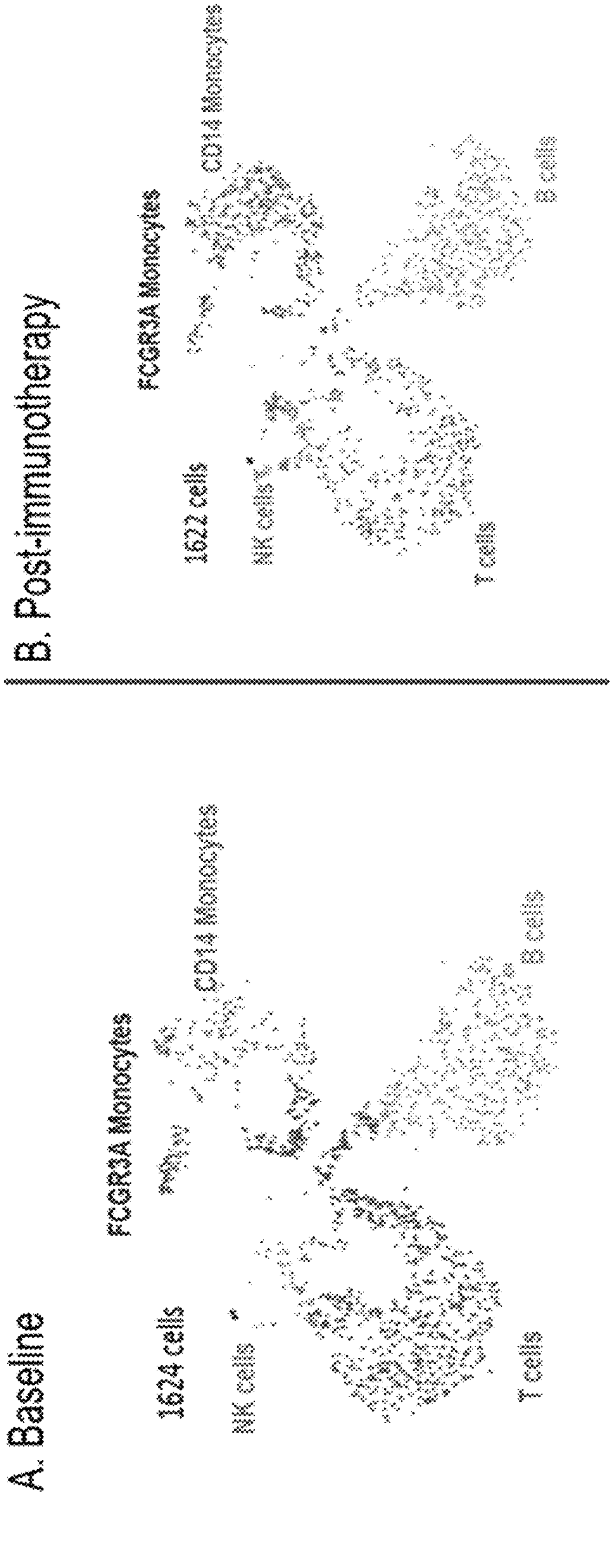
FIGS. 15A-B

A. Clinical and Experimental Timeline
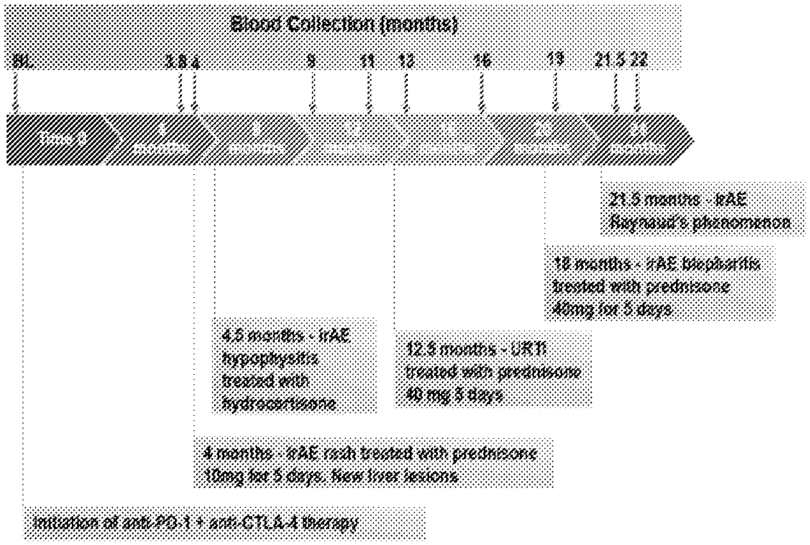
B. Patient with Raynaud's Phenomenon
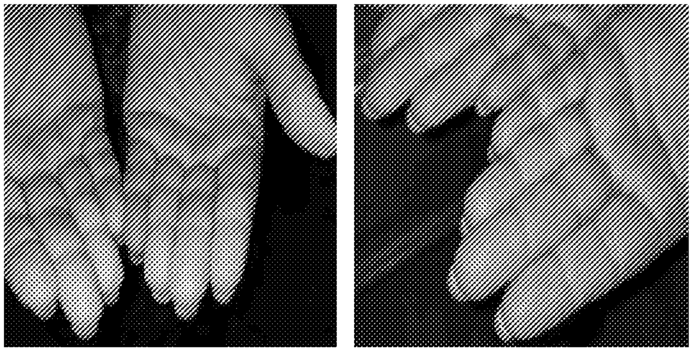
FIGS. 16A-B

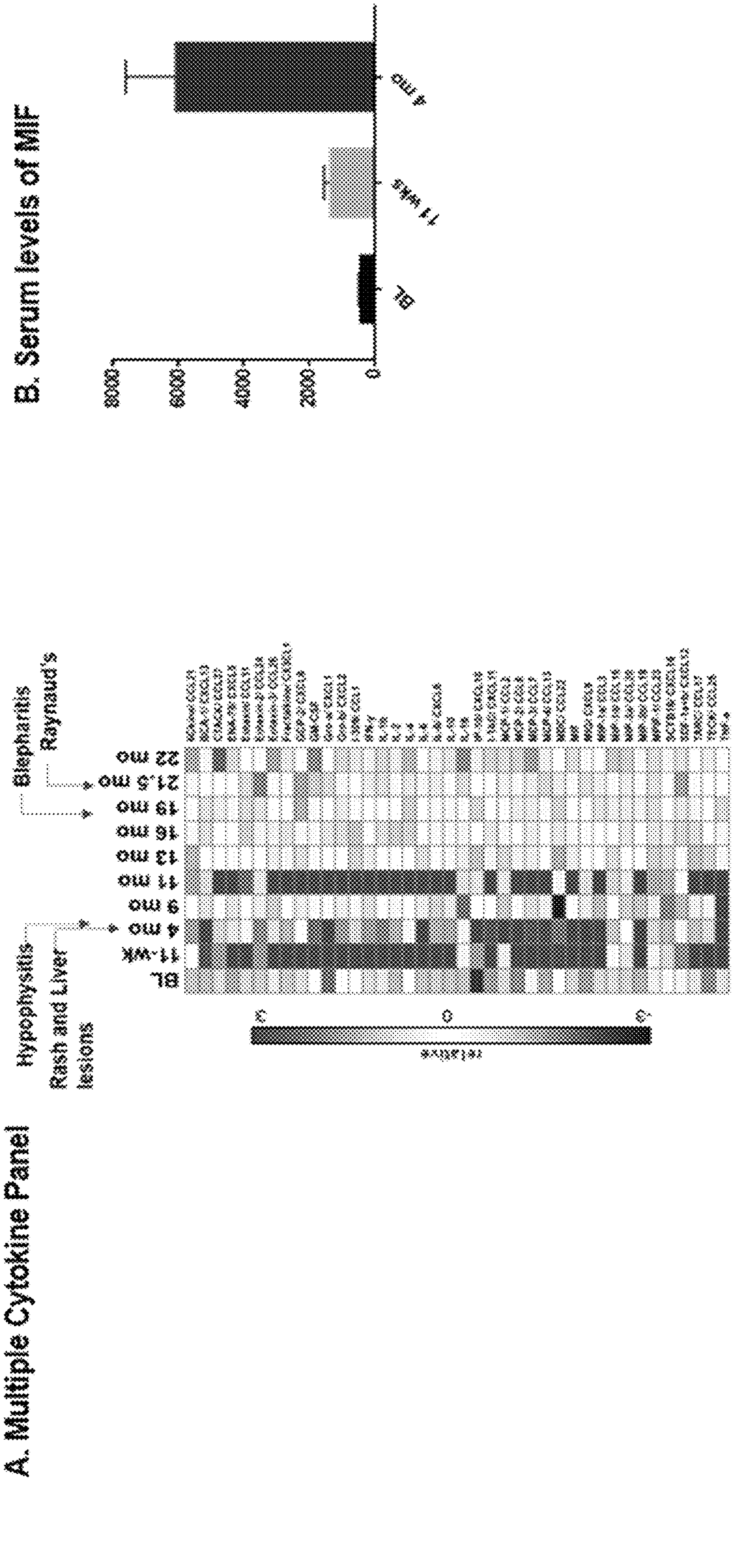
FIGS. 17A-B

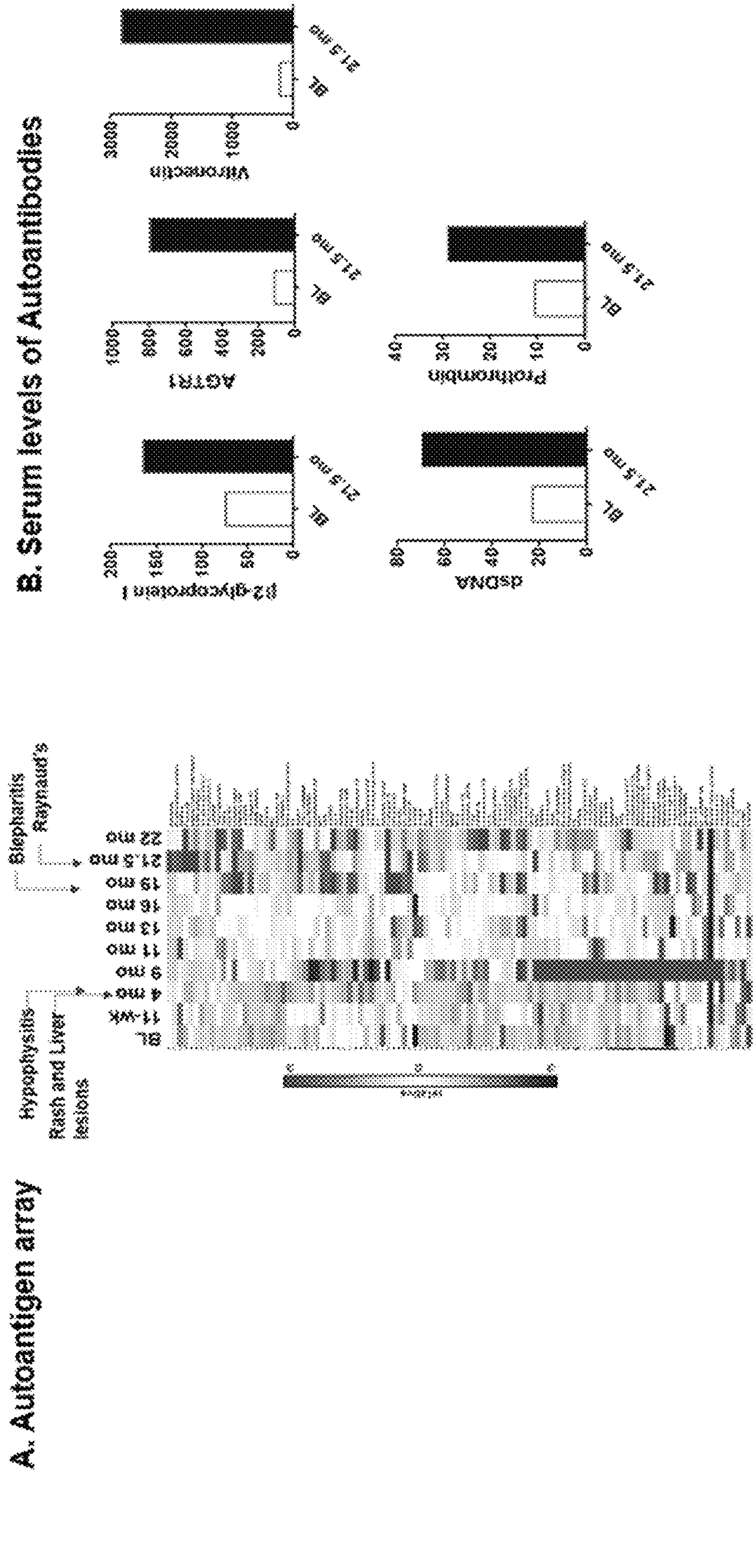
FIGS. 18A-B

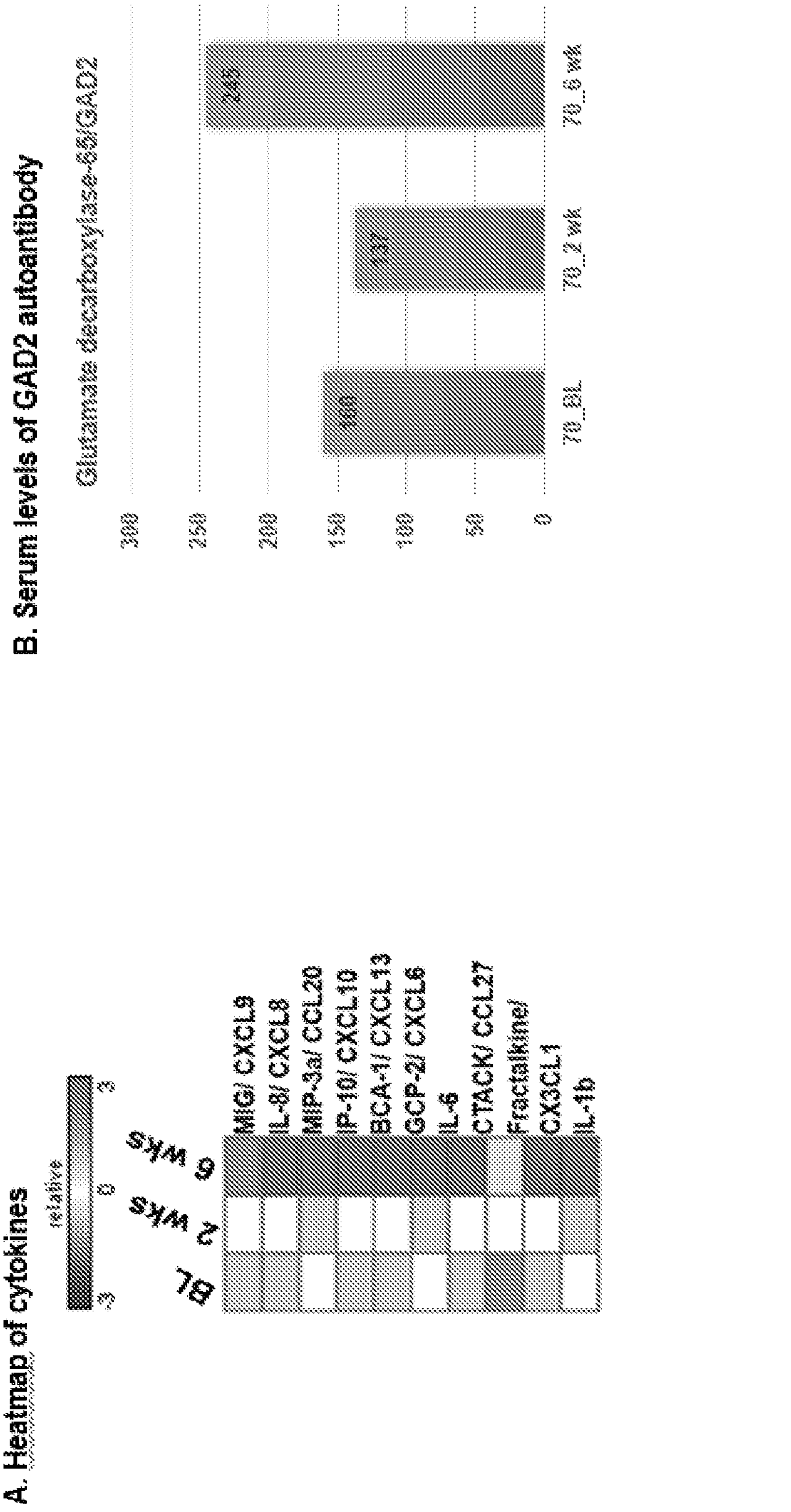
FIGS. 19A-B

PREDICTION AND TREATMENT OF IMMUNOTHERAPEUTIC TOXICITY

PRIORITY CLAIM

This application is a national phase application under 35 U.S.C. § 371 of International Application No. PCT/US2019/026275, filed Apr. 8, 2019, which claims benefit of priority to U.S. Provisional Application Ser. No. 62/654,025, filed Apr. 6, 2018, the entire contents of each of which are hereby incorporated by reference.

BACKGROUND

1. Field of the Disclosure

The present disclosure relates generally to the fields of medicine, oncology, and immunology. More particular, the disclosure relates to identification of markers for immunotherapy-related toxicity in the context of cancer treatments.

2. Background

Cancer immunotherapy has revolutionized the treatment of multiple malignancies, with approvals in melanoma, lung cancer, bladder cancer, head and neck cancer, lymphoma, kidney cancer, Merkel cell tumors, and microsatellite instable cancers. While these promising drugs have led to improved outcomes for thousands of patients, they have also introduced new safety concerns. So-termed immune-related adverse events (irAEs) may affect almost every organ system—including brain, eye, pituitary, skin, thyroid, lung, liver, heart, adrenal, kidney, intestine, and others. In some cases, these autoimmune toxicities may be severe or even permanent. They also may necessitate treatment interruption and prolonged administration of high-dose steroids and other immunosuppressive agents. In contrast to the well-characterized toxicities of cytotoxic chemotherapy and molecularly targeted therapies, immune-related adverse events may occur throughout treatment, with onset as soon as the first treatment cycle or not until months later.

Recent studies indicate that up to 80% of individuals receiving checkpoint therapies experience some form of immune-related adverse event and that about 35% of all patients require systemic corticosteroid treatments to mitigate these events. Further, up to 20% terminate their therapy due to immune-related adverse events (Horvat et al., 2015). These adverse responses convey substantial morbidity, incur considerable costs, and in some cases may preclude further use of these drugs. As immunotherapy use expands from major centers to smaller, isolated, and less experienced sites, the ability to recognize and treat immune-related adverse events promptly may be challenged. Further increasing risk of these toxicities is the emergence of combination immunotherapy regimens, for which the prevalence and severity of immune-related adverse events exceeds those of monotherapy treatments (Wolchok et al., 2013; Postow et al., 2015).

To date, research into immunotherapy biomarkers has focused largely on prediction of efficacy. These efforts have almost exclusively investigated tumor characteristics, such as programmed death ligand 1 (PDL1) expression, mutational burden, and mismatch repair deficiency. Thus far, little is known about who is at risk for autoimmune toxicities or when they will occur, which are concerns that seem more likely related to the characteristics of the patients' immune system rather than to tumor features. Indeed, the only established approach to limiting immune-related adverse events has been the near universal exclusion of patients with autoimmune disease from cancer immunotherapy clinical trials, a practice that may impact a substantial proportion of cancer populations (Khan et al., 2016).

SUMMARY

Thus, in accordance with the present disclosure, there is provided a method of predicting/diagnosing immunotherapeutic toxicity in a human subject comprising (a) providing a chemokine- and/or cytokine-containing sample from said subject; (b) assessing one or more chemokine- and or cytokine levels in said sample; and (c) predicting/diagnosing immunotherapy toxicity in said subject when the level of one or more chemokine and/or cytokine is increased from than populational average, and predicting lack of immunotherapy toxicity in said subject when the level of one or more chemokine and/or cytokine is below populational average.

The sample may be whole blood, serum, plasma, or other body fluid. The immunotherapy toxicity may be cancer immunotherapy toxicity. The one or more chemokine and/or cytokine may be selected from Supplementary Table 1, may be selected from Supplementary Table 1 but excludes GM-CSF and CXCL5, may comprise a plurality or all of the chemokines and/or cytokines of Supplementary Table 1, or may comprise 5, 10, 15, 20, 25, 30, or 35 of the chemokines and/or cytokines of Supplementary Table 1. In particular, one or more cytokine and/or chemokine is (i) MIF35, CXCL16, CCL23, CXCL8, CXCL9, CXCL10, CCL19 and CXCL11, and/or (ii) CXCL9, CXCL10, CXCL11, CCL13, IL-10 and CCL26, and/or (iii) CXCL2, IL-4, IL-6, CXCL8, CXCL10, CXCL11, MIF, CXCL9, CCL3, CCL20, CCL19 and CCL23.

The method may further comprise assessing the level of an autoantibody in the same or a different sample from said subject, and predicting/diagnosing immunotherapy toxicity in said subject when the level of an autoantibody is increased from than populational average, and predicting lack of immunotherapy toxicity in said subject when the level of an autoantibody is below populational average. The autoantibody level may be assessed using a plurality of antigens in Table A, using all antigens in Table A, using a plurality of antigens in Table B, using all antigens in Table B, using a plurality of antigens in Table A and Table B, or using all of antigens in Table A and Table B. The method may further comprise assessing autoantibody levels at a second time point, thereby permitting assessment of a change in immunotherapeutic toxicity risk.

Assessing may comprises ELISA, RIA, Western blot, microarray, bead array, cartridges, lateral flow, or line-probe assays. The method may further comprise repeating steps (a)-(c) at a second time point, thereby permitting assessment of a change in immunotherapeutic toxicity risk. The method may further comprise performing a control reaction with one known chemokine and/or cytokine standards. The method may further comprise treating said subject with a cancer immunotherapy when one or more chemokine and/or cytokine levels is found to be below populational average. The method may further comprise treating said subject with a non-immunotherapy cancer treatment when one or more chemokine and/or cytokine levels is found to be above populational average.

The method may further comprise treating said subject with a cancer immunotherapy and a toxicity mitigating therapy, such as corticosteroids (e.g., prednisone, methylprednisolone, dexamethasone, budesonide), TNF inhibitors (e.g., infliximab), or hormone replacement (e.g., hydrocortisone, levothyroxine) when one or more chemokine and/or cytokine levels are above populational average. The immunotherapy may comprise administration of an immune checkpoint inhibitor, a chimeric antigen receptor, or an immunotoxin. The immunotherapy may comprise administration of an anti-CTLA4 antibody, an anti-PD1 antibody, or an anti-PD1 ligand. The immunotherapy may comprise a combination of multiple immunotherapeutic agents. The immunotherapy may comprise a combination of an immunotherapeutic agent and a non-immunotherapeutic agent.

The subject may have previously been diagnosed with an autoimmune disease. The subject may have not previously been diagnosed with an autoimmune disease. The subject may have lung cancer, melanoma, head & neck cancer, kidney cancer, or lymphoma, or bladder cancer. The subject may be further characterized as receiving a molecular targeted therapy, a chemotherapy, a chemoembolization, a radiotherapy, a radiofrequency ablation, a hormone therapy, a bland embolization, a surgery, or a second distinct immunotherapy. The method may further comprise assessing a rate of increase or decrease in chemokine and/or cytokine levels. The method may further comprise stratifying said subject as having a relatively greater or lesser risk of immunotherapy toxicity based on the number of different chemokine and/or cytokines with elevated levels, with a great number of elevated levels correlating with greater immunotherapy toxicity risk. The method may further comprise selecting a mitigating/adjunct therapy based on the greater or lesser immunotherapy toxicity risk.

In another embodiment, there is provided a method of treating a human subject with cancer comprising (a) providing a chemokine- and or cytokine-containing sample from said subject; (b) assessing one or more chemokine and or cytokine levels in said sample; and (c) treating said subject with (i) a cancer immunotherapy when a chemokine and or cytokine level is found to be below populational average; (ii) a non-immunotherapy cancer treatment when a chemokine- and or cytokine level is found to be above populational average; or (iii) a cancer immunotherapy and a immunotherapy toxicity mitigating therapy when a chemokine- and or cytokine level is found to be above populational average.

The sample may be whole blood, serum, plasma, or other body fluid. The one or more chemokine and/or cytokine may be selected from Supplementary Table 1, may be selected from Supplementary Table 1 but excludes GM-CSF and CXCL5, may comprise a plurality or all of the chemokines and/or cytokines of Supplementary Table 1, or may comprise 5, 10, 15, 20, 25, 30, or 35 of the chemokines and/or cytokines of Supplementary Table 1. In particular, one or more cytokine and/or chemokine is (i) MIF35, CXCL16, CCL23, CXCL8, CXCL9, CXCL10, CCL19 and CXCL11, and/or (ii) CXCL9, CXCL10, CXCL11, CCL13, IL-10 and CCL26, and/or (iii) CXCL2, IL-4, IL-6, CXCL8, CXCL10, CXCL11, MIF, CXCL9, CCL3, CCL20, CCL19 and CCL23.

The method may further comprise assessing the level of an autoantibody in the same or a different sample from said subject, and predicting/diagnosing immunotherapy toxicity in said subject when the level of an autoantibody is increased from than populational average, and predicting lack of immunotherapy toxicity in said subject when the level of an autoantibody is below populational average. The autoantibody level may be assessed using a plurality of antigens in Table A, using all antigens in Table A, using a plurality of antigens in Table B, using all antigens in Table B, using a plurality of antigens in Table A and Table B, or using all of antigens in Table A and Table B. The method may further comprise assessing autoantibody levels at a second time point, thereby permitting assessment of a change in immunotherapeutic toxicity risk.

Assessing may comprises ELISA, RIA, Western blot, microarray, bead array, cartridges, lateral flow, or line-probe assays. The method may further comprise repeating steps (a)-(c) at a second time point, thereby permitting assessment of a change in immunotherapeutic toxicity risk. The adjunct therapy may be a corticosteroid (e.g., prednisone, methylprednisolone, dexamethasone, budesonide), TNF inhibitor (e.g., infliximab), or hormone replacement therapy (e.g., hydrocortisone, levothyroxine). The immunotherapy may comprise administration of an immune checkpoint inhibitor, a chimeric antigen receptor, or an immunotoxin. The immunotherapy may comprise administration of an anti-CTLA4 antibody, an anti-PD1 antibody, or an anti-PD1 ligand. The immunotherapy may comprise a combination of multiple immunotherapeutic agents. The immunotherapy may comprise a combination of an immunotherapeutic agent and a non-immunotherapeutic agent.

The subject may have previously been diagnosed with an autoimmune disease. The subject may have not previously been diagnosed with an autoimmune disease. The subject may have lung cancer, melanoma, head & neck cancer, kidney cancer, or lymphoma, or bladder cancer. The method may further comprise assessing a rate of increase or decrease in chemokine and/or cytokine levels. The method may further comprise stratifying said subject as having a relatively greater or lesser risk of immunotherapy toxicity based on the number of different chemokine and/or cytokines with elevated levels, with a great number of elevated levels correlating with greater immunotherapy toxicity risk. The method may further comprise selecting a mitigating/adjunct therapy based on the greater or lesser immunotherapy toxicity risk.

The method may further comprise classifying immunotherapy toxicity based on organ or organ system in said subject. The organ or organ system may be skin (e.g., dermatitis), lung (e.g., pneumonitis), central/peripheral nervous system (e.g., encephalitis, myasthenia gravis), pituitary gland (e.g., hypophysitis), eye (endophthalmitis), heart (carditis), gastrointestinal tract (colitis), thyroid (thyroiditis/hyperthyroidism/hypothyroidism), adrenal gland (adrenalitis/adrenal insufficiency), liver (hepatitis), pancreas (pancreatitis, autoimmune type 1 diabetes), or kidney (nephritis). The subject may be further characterized as receiving a molecular targeted therapy, a chemotherapy, a chemoembolization, a radiotherapy, a radiofrequency ablation, a hormone therapy, a bland embolization, a surgery, or a second distinct immunotherapy.

A method of determining whether a subject has recovered from immunotherapy toxicity comprising (a) providing a first chemokine- and/or cytokine-containing sample from said subject following immunotherapy and the development of immunotherapy toxicity; (b) assessing chemokine and/or cytokine levels in said first antibody-containing sample; (c) providing a second chemokine- and/or cytokine-containing sample from said subject after immunotherapy toxicity has subsided; (d) assessing chemokine and/or cytokine levels in said second antibody-containing sample; and (e) classifying said subject as suitable for further immunotherapy when one or more chemokine and/or cytokine levels have dropped by at least 50% in said second chemokine- and/or cytokine-containing sample as compared to said first chemokine- and/or cytokine-containing sample.

The method may further comprise treating said subject with an immunotherapy following step (e) when one or more chemokine and/or cytokine levels have dropped by at least 50% in said second chemokine and/or cytokine-containing sample as compared to said first chemokine and/or cytokine-containing sample.

The sample may be whole blood, serum, plasma, or other body fluid. The immunotherapy toxicity may be cancer immunotherapy toxicity. The one or more chemokine and/or cytokine may be selected from Supplementary Table 1, may be selected from Supplementary Table 1 but excludes GM-CSF and CXCL5, may comprise a plurality or all of the chemokines and/or cytokines of Supplementary Table 1, or may comprise 5, 10, 15, 20, 25, 30, or 35 of the chemokines and/or cytokines of Supplementary Table 1. In particular, one or more cytokine and/or chemokine is (i) MIF35, CXCL16, CCL23, CXCL8, CXCL9, CXCL10, CCL19 and CXCL11, and/or (ii) CXCL9, CXCL10, CXCL11, CCL13, IL-10 and CCL26, and/or (iii) CXCL2, IL-4, IL-6, CXCL8, CXCL10, CXCL11, MIF, CXCL9, CCL3, CCL20, CCL19 and CCL23.

The method may further comprise assessing the level of an autoantibody in the same or a different sample from said subject, and predicting/diagnosing immunotherapy toxicity in said subject when the level of an autoantibody is increased from than populational average, and predicting lack of immunotherapy toxicity in said subject when the level of an autoantibody is below populational average. The autoantibody level may be assessed using a plurality of antigens in Table A, using all antigens in Table A, using a plurality of antigens in Table B, using all antigens in Table B, using a plurality of antigens in Table A and Table B, or using all of antigens in Table A and Table B. The method may further comprise assessing autoantibody levels at a second time point, thereby permitting assessment of a change in immunotherapeutic toxicity risk. Assessing may comprises ELISA, RIA, Western blot, microarray, bead array, cartridges, lateral flow, or line-probe assays.

The method may further comprise repeating steps (a)-(c) at a second time point, thereby permitting assessment of a change in immunotherapeutic toxicity risk. The method may further comprise performing a control reaction with one or more known chemokine and/or cytokine standards. The immunotherapy may comprise administration of an immune checkpoint inhibitor, a chimeric antigen receptor, or an immunotoxin. The immunotherapy may comprise administration of an anti-CTLA4 antibody, an anti-PD1 antibody, or an anti-PD1 ligand. The immunotherapy may comprise a combination of multiple immunotherapeutic agents. The immunotherapy may comprise a combination of an immunotherapeutic agent and a non-immunotherapeutic agent.

The subject may have previously been diagnosed with an autoimmune disease. The subject may have not previously been diagnosed with an autoimmune disease. The subject may have lung cancer, melanoma, head & neck cancer, kidney cancer, or lymphoma, or bladder cancer. The method may further comprise assessing a rate of decrease in one or more chemokine and/or cytokine levels. The method may further comprise stratifying said subject as having a relatively greater or lesser risk of recurrent immunotherapy toxicity based on the number of different chemokine and/or cytokine elevations, with a great number of elevations correlating with great risk of recurrent immunotherapy toxicity.

The method may further comprise selecting a mitigating/adjunct therapy based on the greater or lesser immunotherapy toxicity. The adjunct therapy may be a corticosteroid (e.g., prednisone, methylprednisolone, dexamethasone, budesonide), TNF inhibitor (e.g., infliximab), or hormone replacement therapy (e.g., hydrocortisone, levothyroxine). The subject may be further characterized as receiving a molecular targeted therapy, a chemotherapy, a chemoembolization, a radiotherapy, a radiofrequency ablation, a hormone therapy, a bland embolization, a surgery, or a second distinct immunotherapy.

When used herein, the term "populational average" may refer to the population at large, i.e., meaning all patients in the local, regional or national population in which the subject resides. The term may also refer to all cancer patients in the local, regional or national population in which the subject resides, including particular cancer subtypes of the patient. The term may also refer to all healthy patients in the local, regional or national population in which the subject resides. Alternatively, rather than utilized a populational average, the measure of risk may be associated with 1 or 2 standard deviations of value for the populational average, or the top ⅓ of a population's measured systemic cytokine/chemokine levels.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

It is contemplated that any method or composition described herein can be implemented with respect to any other method or composition described herein. Other objects, features and advantages of the present disclosure will become apparent from the following detailed description. It should be understood, however, that the detailed description and the specific examples, while indicating specific embodiments of the invention, are given by way of illustration only, since various changes and modifications within the spirit and scope of the disclosure will become apparent to those skilled in the art from this detailed description.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

(FIG. 1A) Heatmap showing comparisons of 38 cytokine/chemokines in 13 healthy controls (2-weeks apart) and 47 cancer patients (BL, 2/3 weeks and 5/6/7 weeks post-immunotherapy). (FIG. 1B) Serum concentration of CXCL9, CXCL10, CXCL11 and CXCL13 in patients (n=47) at baseline (white boxes) and 2-week post-immunotherapy (Blue boxes). (FIG. 1C) Serum concentration of CXCL9, CXCL10, CXCL11 and CXCL13 in patients (n=47) at baseline (white boxes) and 6-week post-immunotherapy (Blue boxes). All changes are statistically significant ($P<0.05$). Median of each group and p-value was calculated using the Mann-Whitney U test. (FIG. 1D) Heatmap of significantly upregulated cytokines and chemokines in cancer patients that did not develop toxicity compare to healthy controls ($P<0.05$). (FIG. 1E) Heatmap of significantly upregulated cytokines and chemokines in cancer patients that developed toxicity versus healthy controls ($P<0.05$).

(FIG. 2A) Heatmap of significantly downregulated cytokines and chemokines in cancer patients that did not develop toxicity (No toxicity group colored in dark brown) versus patients that developed toxicity (Toxicity group in light brown) (P<0.05). (FIG. 2B) Comparison of serum concentration of CXCL9, CXCL10, CXCL11 and CCL19 between two groups of patients at baseline before the initiation of immune checkpoint blockade: Toxicity group in grey and No-toxicity group in blue. All changes are statistically significant (P<0.05). Median of each group and p-value was calculated using the Mann-Whitney U test. (FIG. 2C) Fold change in serum levels of CXCL9 and CXCL10 at 6-weeks post-treatment compared to baseline is calculated between toxicity group (grey) and No-toxicity group (blue). (FIG. 2D) Comparison of total IgG serum conc. in healthy controls (grey), No-toxicity group (blue) and toxicity group (Red) at baseline before the initiation of immune checkpoint blockade. (FIG. 2E) Comparison of total IgG serum conc. at baseline and at 2 weeks post-immunotherapy in healthy controls (grey), No-toxicity group (blue) and toxicity group (Red). Median of each group and p-value was calculated using the Mann-Whitney U test (P<0.05).

FIG. 4. Logistic regression test identifies CXCL8, MIF35, CXCL16 and CCL23 as important predictors.

FIGS. 14A-D. Single cell RNA sequencing (ScRNA-seq) of Peripheral Blood Mononuclear cells (PBMCs) using Biorad-Illumina-ddseq instrument. (FIG. 14A) PBMCs from a healthy patient were isolated and run on Single-Cell Workflow. The Seurat tutorial for Principal Component Analysis (PCA) was used to cluster the cells, which are displayed on a t-SNE (t-Distributed Stochastic Neighbor Embedding) plot. Percentages indicate the percentage of the subpopulation to the total number of cells. (FIG. 14B) Heat map showing the top 10 genes for each cluster ranked by log-fold change. Genes were statistically determined by comparing the cells in each cluster to all other cells. (FIG. 14C) ScRNA-seq and Canonical Correspondence Analysis (CCA) analysis of fresh versus frozen PBMCs from the same subject. (FIG. 14D) The t-SNE is labeled by sample type, fresh or frozen. Each cluster has a similar number of cells in the fresh and the frozen sample.

FIGS. 15A-B. Single cell RNA sequencing (ScRNA-seq) of Peripheral Blood Mononuclear cells (PBMCs) using 10× chromium technologies. PBMCs were run through 10× Chromium ScRNA-seq Workflow and CellRanger Pipeline. Principal Component Analysis (PCA) was used to cluster the cells, which are displayed on a t-SNE (t-Distributed Stochastic Neighbor Embedding) plot and viewed in Loupe Browser. PBMCs were isolated from a single patient at Baseline and 6 weeks post-immunotherapy. Approx. 1600 cells per sample were run through chromium ScRNA-seq workflow and sequenced on Hiseq 2500 generating approx. 50,000 reads high quality reads with phred score>30. Data was analyzed using CellRanger Pipeline and visualized using Loupe browser and is displayed on a t-SNE plot. This data demonstrates the feasibility of carrying out ScRNA-seq experiments using 10× chromium on frozen PBMCs as proposed in our applications. Preliminary analysis shows increase in CD14 positive monocytes after immunotherapy initiation.

FIGS. 16A-B. (FIG. 16A) Timeline of clinical events and specimen collection points. (FIG. 16B) Images of patient's Raynaud's phenomena during cold and rewarming.

FIGS. 17A-B. (FIG. 17A) Heatmap of 40 cytokine levels at 10 time-points. (FIG. 17B) Serum concentrations of Macrophage migration inhibitory factor (MIF) at baseline (BL) before the initiation of immune checkpoint therapy (ICI) and at 11 weeks and 4 month (4 mo) post-immunotherapy. Data points represent average of two independent experimental runs. Error bars represent means±standard deviation.

FIGS. 18A-B. (FIG. 18A) Heatmap of 124 autoantibodies at 10 time-points. (FIG. 18B) Serum levels of selected autoantibodies upregulated at the time of development of Raynaud's phenomenon compared to baseline levels. Values on y-axis represents net fluorescence intensity (NFI) as described in methods.

FIGS. 19A-B. (FIG. 19A) Heatmap of cytokines upregulated at 6-week post-immunotherapy. (FIG. 19B) Serum levels of Glutamate decarboxylase-65/GAD2 autoantibodies upregulated at the time of development of type I diabetes compared to baseline levels. Values on y-axis represents net fluorescence intensity (NFI) as described in methods.

DESCRIPTION OF ILLUSTRATIVE EMBODIMENTS

Figure 1:
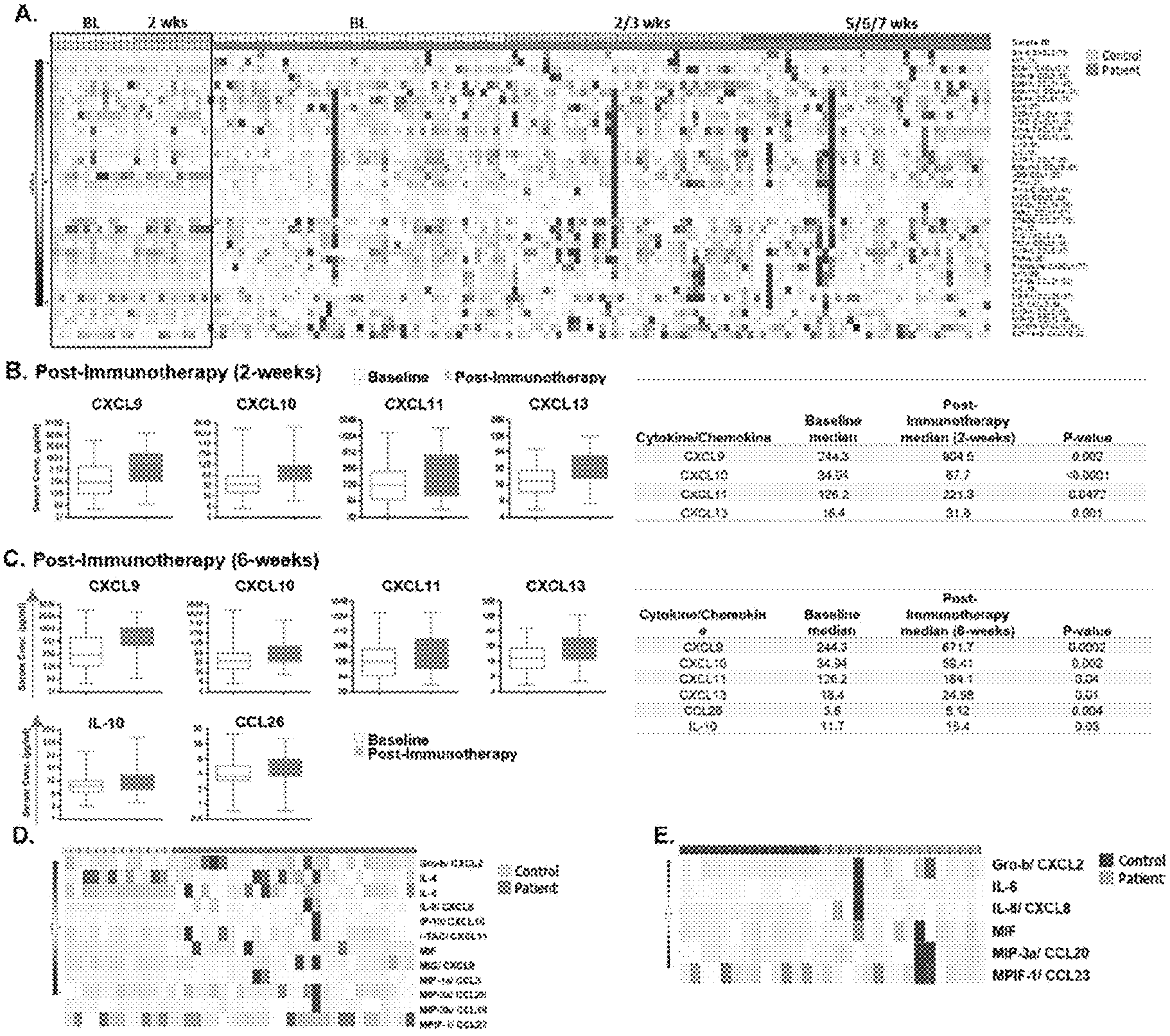
FIGS. 1A-E.

As discussed above, the advent of new oncotherapies, in particular immunotherapies, has greatly expanded the arsenal of tools with which oncologists can attack cancer. And while these new drugs have led to improved outcomes for thousands of patients, they have also introduced new safety concerns. In earlier studies, the inventors demonstrated that more than one-quarter of healthy individuals have strong humoral responses to a variety of self-antigens, indicating that "quiescent" autoimmunity is much more common than clinically manifest autoimmune disease (Li et al., 2007; 2010; 2011; Tan et al., 1997; Abiola et al., 2003; Wandstrat et al., 2006; Olsen and Karp, 2014). These findings indicate that immune tolerance within the human population varies quantitatively and that a significant fraction of cancer patients have pre-existing autoimmunity that does not progress to autoimmune disease due to undefined regulatory mechanisms.

In the present study, the inventors categorized immune function by analyzing (i) a panel of more than 40 cytokines/chemokines, and (ii) total IgG levels. Serum was collected from patients treated with immune checkpoint inhibitors at multiple time-points: pre-treatment, at 2-3 weeks, and at 6 weeks. Baseline and dynamic cytokine profiles were determined using a multiplex panel. Total IgG was determined using ELISA. The association between these biomarkers and the presence of irAEs was then analyzed using t tests and ANOVA.

A total of 78 subjects were enrolled, including 65 cancer patients receiving immune checkpoint inhibitors, along with 13 healthy controls. Mean age was 65 years, 55% were women, and 83% had lung cancer. Immune-related AEs occurred in 35% of cases as follows: pneumonitis (n=11), endocrinopathy (n=6), dermatitis (n=2), arthritis (2), encephalitis (1), complex (2). Among the 40 cytokines measured, 14 were significantly upregulated in cancer patients at baseline compared to healthy controls. There were significant systemic increases in chemokines CXCL9, CXCL10, CXCL11 and CXCL13 in patients at 2 weeks post-immunotherapy and six cytokines/chemokines including CXCL9, CXCL10, CXCL11, CXCL13, IL-10, and CCL26 at 6 weeks post treatment. Patients who developed irAEs had significantly lower systemic levels of CXCL9, CXCL10, CXCL11 and CCL19 at baseline and exhibited far greater increases in CXCL9 and CXCL10 levels at 6 weeks post treatment compared to patients without irAEs. Baseline total serum IgG levels were significantly lower in patients who developed irAEs. Thus, patients who developed irAEs had lower baseline levels and greater post-treatment increases in multiple cytokine levels, as well as lower baseline levels in total IgG. These findings indicate that immune dysregulation and adverse immune responses elicited by checkpoint inhibitory therapy is associated with pre-existing characteristics of the systemic immune system of cancer patients, suggesting that an analysis of the immune system prior to the initiation of therapy can identify individuals with increased risk for irAEs.

These and other aspects of the disclosure are described in detail below.

I. IMMUNOTHERAPY AND RELATED TOXICITY

The emergence of cancer immunotherapy has introduced an entirely new set of unpredictable, potentially severe, and possibly permanent toxicities. Immune checkpoint inhibitors targeting the cytotoxic T lymphocyte antigen 4 (CTLA4) and programmed death 1 (PD1) axes are transforming cancer treatment, with impressive clinical activity already leading to FDA approvals for melanoma, non-small cell lung cancer, renal cell carcinoma, Hodgkin's lymphoma, and bladder cancer. However, cancer immunotherapies also pose a risk for immune-related adverse events (irAEs). These diverse toxicities are problematic because they are entirely distinct from the toxicities oncologists have come to expect with conventional chemotherapy and molecularly targeted therapies.

Immune-mediated toxicities may impact almost every organ system, including brain, pituitary, thyroid, ocular, pulmonary, hepatic, intestinal, dermatologic, and adrenal (Topalian et al., 2012). In contrast to the well-characterized temporal patterns of classic chemotherapy toxicities such as alopecia, nausea/vomiting, and myelosuppression, the onset and duration of irAEs remains unpredictable. Recent studies indicate that up to 80% of individuals receiving checkpoint therapies experience some form of irAE, with about 35% of all patients requiring systemic corticosteroid treatments to mitigate these events, and up to 20% terminating their therapy due to irAEs (Horvat et al., 2015). These adverse responses convey substantial morbidity, incur considerable costs, and in some cases may preclude further use of these drugs. As immunotherapy use expands from major centers where pivotal trials have been conducted to smaller, isolated, and less experienced community sites, the ability to recognize and treat irAEs promptly may be challenged. With the FDA approval of combination PD1 and CLTA4 inhibition for melanoma in October 2015, and similar combinations currently under study in other diseases, rates and severity of irAEs may be even greater in the future. To date, no clinical, laboratory, or radiographic biomarkers can predict these toxicities.

The CTLA4 and PD1-PDL1 axes normally function to activate regulatory pathways that maintain peripheral tolerance to self-antigens (Allison et al., 1998a). The therapeutic benefit of inhibiting these regulatory systems is thought to result from the amplification of suppressed anti-tumor immune responses that are blocked by tumor-specific manipulations of the immune system (Gubin et al., 2014). However, these regulatory pathways are also intimately involved in the regulation of autoimmune and auto-aggressive immune responses (Allison et al., 1998b). As a result, it is quite likely that any extant autoimmune responses that are being regulated by these peripheral pathways might also become activated during checkpoint blockade therapy.

Autoimmune disease, in which the recognition of self-antigens by the immune system leads to severe damage to specific self-tissues, is estimated to affect almost 10% of the U.S. population (Cooper et al., 2009). A recent SEER-Medicare analysis suggests that the prevalence of these conditions may be even higher among individuals with cancer (Khan et al., 2016). Moreover, recent studies by the inventors and others have found that more than 26% of healthy individuals have strong IgG humoral immune responses to a variety of self-antigens, indicating that "benign" autoimmunity is much more common than autoimmune disease (FIG. 1) (Wandstradt et al., 2006; Li et al., 2011; Li and Wakeland, 2015; Tan et al., 1997). These findings indicate that many healthy individuals exhibit significant autoimmunity that is regulated in the peripheral immune system by pathways such as those triggered by CTLA-4 and PD1. Consistent with this observation, CTLA-4 and PD1 are both known to potentiate autoimmune disease, suggesting that the inhibition of these regulatory pathways aggravates pre-existing autoimmunity (Kristiansen et al., 2000; Romo-Tena et al., 2013; Gianchecchi et al., 2013). Based on this observation, the inventors hypothesize that checkpoint therapy irAEs often result from the activation of pre-existing autoimmunity.

II. AUTOIMMUNITY, AUTOANTIGENS AND CYTOKINES/CHEMOKINES

A. Autoimmunity

Autoimmunity is defined as the system of immune responses of an organism against its own healthy cells and tissues. Any disease that results from such an aberrant immune response is termed an autoimmune disease. Prominent examples include celiac disease, diabetes mellitus type 1, sarcoidosis, systemic lupus erythematosus (SLE), Sjögren's syndrome, eosinophilic granulomatosis with polyangiitis, Hashimoto's thyroiditis, Graves' disease, idiopathic thrombocytopenic purpura, Addison's disease, rheumatoid arthritis (RA), psoriatic arthritis, ankylosing spondylitis, polymyositis (PM), and dermatomyositis (DM). Autoimmune diseases are very often treated with steroids.

The misconception that an individual's immune system is totally incapable of recognizing self-antigens is not new. Paul Ehrlich, at the beginning of the twentieth century, proposed the concept of horror autotoxicus, wherein a "normal" body does not mount an immune response against its own tissues. Thus, any autoimmune response was perceived to be abnormal and postulated to be connected with human disease. Now, it is accepted that autoimmune responses are an integral part of vertebrate immune systems (sometimes termed "natural autoimmunity"), normally prevented from causing disease by peripheral immunoregulatory pathways, such as those triggered through CTLA-4 and PD1.

While a high level of autoimmunity is unhealthy, a low level of autoimmunity may actually be beneficial. Taking the experience of a beneficial factor in autoimmunity further, one might hypothesize with intent to prove that autoimmunity is always a self-defense mechanism of the mammalian system to survive. The system does not randomly lose the ability to distinguish between self and non-self; the attack on cells may be the consequence of cycling metabolic processes necessary to keep the blood chemistry in homeostasis.

Certain individuals are genetically susceptible to developing autoimmune diseases. This susceptibility is associated with multiple genes plus other risk factors. Genetically predisposed individuals do not always develop autoimmune diseases, but often have immune systems that are imbalanced towards a pro-inflammatory phenotype. Many different risk alleles have been shown to contribute to susceptibility to autoimmunity and these alleles are commonly present at significant frequencies in normal human populations. The MHC complex is among the most potent genetic risk factors for virtually all autoimmune diseases. However, the development of autoimmunity typically requires the presence of multiple risk alleles within an individual's genome. Thus, individuals with a benign autoimmunity commonly have several risk alleles for autoimmunity but lack a sufficient number to develop disease or have not been exposed to a sufficient environmental stimulation to elicit the development of autoimmune disease. Thus, although their immune systems can be shown to have specific inflammatory characteristics, for example abnormal levels of systemic cytokines, or antibodies that detect self-antigens, there are no significant clinical disease manifestations.

A person's sex also seems to have some role in the development of autoimmunity; that is, most autoimmune diseases are sex-related. Nearly 75% of the more than 23.5 million Americans who suffer from autoimmune disease are women, although it is less-frequently acknowledged that millions of men also suffer from these diseases. The inventors have shown that, among patients with lung cancer, those with autoimmune disease were more likely to be women (Khan et al., 2016). According to the American Autoimmune Related Diseases Association (AARDA), autoimmune diseases that develop in men tend to be more severe. A few autoimmune diseases that men are just as or more likely to develop as women include: ankylosing spondylitis, type 1 diabetes mellitus, granulomatosis with polyangiitis, Crohn's disease, Primary sclerosing cholangitis and psoriasis.

An interesting inverse relationship exists between infectious diseases and some autoimmune diseases. In areas where multiple infectious diseases are endemic, some autoimmune diseases are less frequent. The reverse, to some extent, seems to hold true. The hygiene hypothesis attributes these correlations to the immune manipulating strategies of pathogens. Whilst such an observation has been variously termed as spurious and ineffective, according to some studies, parasite infections are associated with reduced activity of autoimmune disease. The putative mechanism is that the parasite attenuates the host immune response in order to protect itself. This may provide a serendipitous benefit to a host that also suffers from autoimmune disease. The details of parasite immune modulation are not yet known but may include secretion of anti-inflammatory agents or interference with the host immune signaling.

A paradoxical observation has been the strong association of certain microbial organisms with autoimmune diseases. For example, *Klebsiella pneumoniae* and coxsackievirus B have been strongly correlated with ankylosing spondylitis and diabetes mellitus type 1, respectively. This has been explained by the tendency of the infecting organism to produce super-antigens that are capable of polyclonal activation of B-lymphocytes, and production of large amounts of antibodies of varying specificities, some of which may be self-reactive. Thus, for some autoimmune diseases, it is likely that specific infections may be the environmental stimulus that causes the transition from a "benign" autoimmunity to autoimmune disease.

Exposure to certain chemical agents and drugs is also associated with the genesis of autoimmune conditions and are likely to reflect other types of environmental stimuli that can trigger autoimmunity in predisposed individuals. The most striking of these is the drug-induced lupus erythematosus. Usually, withdrawal of the offending drug cures the symptoms in a patient. Cigarette smoking is now established as a major risk factor for both incidence and severity of rheumatoid arthritis. This may relate to abnormal citrullination of proteins, since the effects of smoking correlate with the presence of antibodies to citrullinated peptides.

B. Autoantigen Microarray Super Panel (128 Antigen Panel)

An autoantigen is defined as normal protein or protein complex (and sometimes DNA or RNA) that is recognized by the immune system of patients suffering from a specific autoimmune disease. These antigens should not be, under normal conditions, the target of the immune system, but their associated T cells are not deleted and instead attack.

Autoantigen array super panel I contains 128 autoantigens and various internal controls. The autoantigens in this panel include most of nuclear antigens, cytoplasmic antigens, membrane antigen, phospholipid antigens, as well as some novel autoantigens identified from serum and tissues. The antigens in the Super Panel are listed below:

TABLE A

| Autoantigen SuperPanel | | | | |
|---|---|---|---|---|
| Cardolipin | DGPS | Heparan HSPG | Nup62 | SP100 |
| CENP-A | dsDNA | Heparin | PCNA | Sphingomyelin |
| CENP-B | EBNA1 | Heperan Sulfate | Peroxiredoxin 1 | SRP54 |
| Chondroitin Sulfate C | Elastin | Histone-total | Phophatidylinositol | ssSDNA |
| Chromatin | Entaktin EDTA | human genomic DNA | PL-12 | ssRNA |
| Collagen I | Factor I | Intrinsic Factor | PL-7 | T1F1 GAMMA |
| Collagen II | Factor P | Jo-1 | PM/Scl-100 | Thyroglobulin |
| Collagen III | FactorB | KU (P70/P80) | PM/Scl-75 | TNFa |
| Collagen IV | FactorD | La/SSB | POLB | Topoisomerase 1 |
| Collagen V | FactorH | Laminin | PR3 | TPO |
| Collagen VI | Fibrinogen IV | LC1 | Proteoglycan | TTG |
| complement C1q | Fibrinogen S | LKM1 | Prothrombin protien | U1-snRNP-68 |
| complement C3 | Fibronectin | M2 Antigen | Ribo phaspho protein P1 | U1-snRNP-A |
| complement C3a | GBM (disso) | Matrigel | Ribo phaspho protein P2 | U1-snRNP-BB' |
| complement C3b | Gliadin (IgG) | MDAS | Ribo phasphoprotein P0 | U1-snRNP-C |
| complement C4 | Glycated Albumin | Mi-2 | Ro/SSA (52 KDa) | Vimentin |
| anti-Ig | IgG Control | β2-microglobulin | β2-glycoprotein 1 | Vitronectin |

The autoantigens are printed on 16-pad FAST slide. Each chip contains 16 identical arrays and can process 15 samples and one PBS control.

TABLE B

| Autoantigen Microarray Panel IV | | |
|---|---|---|
| CMV-G | Beef_Bos taurus | ubiquitin-like modifier activating anzyme 2(UBA2) |
| CMV-M | Shrimp_Penacidae | NY-ESO-1 |
| CMV EXT-2 | Peanut_Arachis hypogaea | Prostatic Acid Phosphatase |
| CMV GRADE III | Wheat, Whole_Triticum aestivum | Prostate Specific Membrane Antigen |
| HEPATITIS A | Mite, House Dust_Blomia tropicalis | MAGEA3 |
| HAV CONCENTRATE | Bermuda_Cynodon dactyion | FOLH1 |
| HSV-1 | Cedar, Red_Juniper rus virginiana | PSA |
| HSV-2 | Plantain, English_Plantago lanceolata | CA 125 |
| RUBEOLA | Honey Bee_Apis mellifera | CEA |
| RSV | 3-hydroxy-3-methylglutaryl-coenzyme A reductase | PSMA/FOLH1/NAALADase 1 |
| ROTAVIRUS SA-11 | Aminoacyl-tRNA Synthetase | Myosin Light Chain |
| RUBELLA VIRUS GRADE III | Asparaginyl-tRNA Synthetase(KS) | Muscarinic receptor |
| RUBELLA VIRUS GRADE IV | Glycyl-tRNA Synthetase(E3) | Albumin Bovine fraction V |
| RUBELLA GRADE IV | Lysyl-tRNA Synthetase | AQP4 |
| RSVP | Phenylalanyl-tRNA Synthetase 2 | ONA Polymerase beta Protein |
| TOXOPLASMA Antigen | Human Cytosolic 5'-nucleotidase 1A | EBV EBNA1 |
| VZV | glutaminyl-tRNA Synthetase | AGTR1(angiotension receptor1) |
| VZV GRADE II | MORC family CW-type zinc finger 3 (MORC3) | Collagenase A |
| HUMAN AZUROCDIN | signal recognition particle 14 kDa | Collagenase D |
| House Dust | SUMO1 activating enzyme subunit 1(SAE1) | Tetanus toxin |
| Dog Dander | tryptophanyl-tRNA Synthetase(WARS) | Ig Control |
| Dog Epithella | tyrosyl-tRNA Synthetase(YARS) | Anti-Ig |

The autoantigens, are printed on 16-pad FAST slide. Each chip contains 16 identical arrays and can process 15 samples and one PBS control.

C. Cytokines/Chemokines

Cytokines are a broad category of small proteins (~5-20 kDa) that are important in cell signaling. Their release has an effect on the behavior of cells around them. Cytokines are involved in autocrine signaling, paracrine signaling and endocrine signaling as immunomodulating molecules. Cytokines may include chemokines, interferons, interleukins, lymphokines, and tumor necrosis factors but generally not hormones or growth factors (despite some overlap in the terminology). Cytokines are produced by a variety of cell types including immune cells like macrophages, monocytes, dendritic cells, B lymphocytes, T lymphocytes and mast cells, as well as endothelial cells, fibroblasts, and various stromal cells; a given cytokine may be produced by more than one type of cell.

Cytokines act through receptors and modulate the balance between humoral and cell-based immune responses, and they regulate the maturation, growth, and responsiveness of several cell populations. Some cytokines enhance or inhibit the action of other cytokines in complex ways. They are important in health and disease, specifically in host responses to infection, immune responses, inflammation, autoimmunity, trauma, sepsis, cancer, and reproduction. The modulation of cytokines levels for immune cytokines such as TNF, IL6, IL2, etc. are a standard and FDA approved strategy for the treatment of autoimmunity, cancer and other diseases.

Cytokines have been classified as lymphokines, interleukins, and chemokines (discussed further below), based on their presumed function, cell of secretion, or target of action. Because cytokines are characterized by considerable redundancy and pleiotropism, such distinctions, allowing for exceptions, are obsolete.

The term “interleukin” was initially used by researchers for those cytokines whose presumed targets are principally leukocytes. It is now used largely for designation of newer cytokine molecules and bears little relation to their presumed function. The vast majority of these are produced by T-helper cells. Lymphokines are produced by lymphocytes, monokines are produced exclusively by monocytes, interferons are involved in antiviral responses, colony stimulating factors support the growth of cells in semisolid media, and chemokines mediate chemoattraction (chemotaxis) between cells.

In recent years, the cytokine receptors have come to demand the attention of more investigators than cytokines themselves, partly because of their remarkable characteristics, and partly because a deficiency of cytokine receptors has now been directly linked to certain debilitating immunodeficiency states. In this regard, and also because the redundancy and pleomorphism of cytokines are, in fact, a consequence of their homologous receptors, many authorities think that a classification of cytokine receptors would be more clinically and experimentally useful.

A classification of cytokine receptors based on their three-dimensional structure has, therefore, been attempted. Such a classification, though seemingly cumbersome, provides several unique perspectives for attractive pharmacotherapeutic targets.

- Immunoglobulin (Ig) superfamily, which are ubiquitously present throughout several cells and tissues of the vertebrate body, and share structural homology with immunoglobulins (antibodies), cell adhesion molecules, and even some cytokines. Examples: IL-1 receptor types.
- Hemopoietic Growth Factor (type 1) family, whose members have certain conserved motifs in their extracellular amino-acid domain. The IL-2 receptor belongs to this chain, whose γ-chain (common to several other cytokines) deficiency is directly responsible for the x-linked form of Severe Combined Immunodeficiency (X-SCID).
- Interferon (type 2) family, whose members are receptors for IFN β and γ.
- Tumor necrosis factors (TNF) (type 3) family, whose members share a cysteine-rich common extracellular binding domain, and includes several other non-cytokine ligands like CD40, CD27 and CD30, besides the ligands on which the family is named (TNF).
- Seven transmembrane helix family, the ubiquitous receptor type of the animal kingdom. All G protein-coupled receptors (for hormones and neurotransmitters) belong to this family. Chemokine receptors, two of which act as binding proteins for HIV (CD4 and CCR5), also belong to this family.
- Interleukin-17 receptor (IL-17R) family, which shows little homology with any other cytokine receptor family. Structural motifs conserved between members of this family include: an extracellular fibronectin III-like domain, a transmembrane domain and a cytoplasmic SERIF domain. The known members of this family are as follows: IL-17RA, IL-17RB, IL-17RC, IL17RD and IL-17RE.

Each cytokine has a matching cell-surface receptor. Subsequent cascades of intracellular signalling then alter cell functions. This may include the upregulation and/or downregulation of several genes and their transcription factors, resulting in the production of other cytokines, an increase in the number of surface receptors for other molecules, or the suppression of their own effect by feedback inhibition.

The effect of a particular cytokine on a given cell depends on the cytokine, its extracellular abundance, the presence and abundance of the complementary receptor on the cell surface, and downstream signals activated by receptor binding; these last two factors can vary by cell type. Cytokines are characterized by considerable "redundancy", in that many cytokines appear to share similar functions.

Inflammatory cytokines have been shown to cause an IL-10-dependent inhibition of T-cell expansion and function by up-regulating PD-1 levels on monocytes, which leads to IL-10 production by monocytes after binding of PD-1 by PD-L.

Adverse reactions to cytokines are characterized by local inflammation and/or ulceration at the injection sites. Occasionally such reactions are seen with more widespread papular eruptions.

As mentioned, one particular type of cytokine is a chemokine. Chemokines are a family of small cytokines, or signaling proteins secreted by cells. Their name is derived from their ability to induce directed chemotaxis in nearby responsive cells; they are chemotactic cytokines.

Cytokine proteins are classified as chemokines according to behavior and structural characteristics. In addition to mediating chemotaxis, chemokines are all approximately 8-10 kilodaltons in mass and have four cysteine residues in conserved locations that are key to forming their 3-dimensional shape.

These proteins have historically been known under several other names including the SIS family of cytokines, SIG family of cytokines, SCY family of cytokines, Platelet factor-4 superfamily or intercrines. Some chemokines are considered pro-inflammatory and can be induced during an immune response to recruit cells of the immune system to a site of infection, while others are considered homeostatic and are involved in controlling the migration of cells during normal processes of tissue maintenance or development. Chemokines are found in all vertebrates, some viruses and some bacteria, but none have been described for other invertebrates.

Chemokines have been classified into four main subfamilies: CXC, CC, CX3C and XC. All of these proteins exert their biological effects by interacting with G protein-linked transmembrane receptors called chemokine receptors that are selectively found on the surfaces of their target cells.

The major role of chemokines is to act as a chemoattractant to guide the migration of cells. Cells that are attracted by chemokines follow a signal of increasing chemokine concentration towards the source of the chemokine. Some chemokines control cells of the immune system during processes of immune surveillance, such as directing lymphocytes to the lymph nodes so they can screen for invasion of pathogens by interacting with antigen-presenting cells residing in these tissues. These are known as homeostatic chemokines and are produced and secreted without any need to stimulate their source cell(s). Some chemokines have roles in development; they promote angiogenesis (the growth of new blood vessels), or guide cells to tissues that provide specific signals critical for cellular maturation. Other chemokines are inflammatory and are released from a wide variety of cells in response to bacterial infection, viruses and agents that cause physical damage such as silica or the urate crystals that occur in gout. Their release is often stimulated by pro-inflammatory cytokines such as interleukin 1. Inflammatory chemokines function mainly as chemoattractants for leukocytes, recruiting monocytes, neutrophils and other effector cells from the blood to sites of infection or tissue damage. Certain inflammatory chemokines activate cells to initiate an immune response or promote wound healing. They are released by many different cell types and serve to guide cells of both innate immune system and adaptive immune system.

Chemokines are functionally divided into two groups:

Homeostatic: are constitutively produced in certain tissues and are responsible for basal leukocyte migration. These include: CCL14, CCL19, CCL20, CCL21, CCL25, CCL27, CXCL12 and CXCL13. This classification is not strict; for example, CCL20 can act also as pro-inflammatory chemokine.

Inflammatory: these are formed under pathological conditions (on pro-inflammatory stimuli, such as IL-1, TNF-alpha, LPS, or viruses) and actively participate in the inflammatory response attracting immune cells to the site of inflammation. Examples are: CXCL-8, CCL2, CCL3, CCL4, CCL5, CCL11, CXCL10.

The main function of chemokines is to manage the migration of leukocytes (homing) in the respective anatomical locations in inflammatory and homeostatic processes.

Basal: homeostatic chemokines are basal produced in the thymus and lymphoid tissues. Their homeostatic function in homing is best exemplified by the chemokines CCL19 and CCL21 (expressed within lymph nodes and on lymphatic endothelial cells) and their receptor CCR7 (expressed on cells destined for homing in cells to these organs). Using these ligands is possible routing antigen-presenting cells (APC) to lymph nodes during the adaptive immune response. Among other homeostatic chemokine receptors include: CCR9, CCR10, and CXCR5, which are important as part of the cell addresses for tissue-specific homing of leukocytes. CCR9 supports the migration of leukocytes into the intestine, CCR10 to the skin and CXCR5 supports the migration of B-cell to follicles of lymph nodes. As well CXCL12 (SDF-1) constitutively produced in the bone marrow promotes proliferation of progenitor B cells in the bone marrow microenvironment.

Inflammatory: Inflammatory chemokines are produced in high concentrations during infection or injury and determine the migration of inflammatory leukocytes into the damaged area. Typical inflammatory chemokines include: CCL2, CCL3 and CCL5, CXCL1, CXCL2 and CXCL8. A typical example is CXCL-8, which acts as a chemoattractant for neutrophils.

In contrast to the homeostatic chemokine receptors, there is significant promiscuity (redundancy) associated with binding receptor and inflammatory chemokines. This often complicates research on receptor-specific therapeutics in this area.

The following provides an association with chemokines and the cells that they attract:

Monocytes/macrophages: the key chemokines that attract these cells to the site of inflammation include: CCL2, CCL3, CCL5, CCL7, CCL8, CCL13, CCL17 and CCL22.

T-lymphocytes: the four key chemokines that are involved in the recruitment of T lymphocytes to the site of inflammation are: CCL2, CCL1, CCL22 and CCL17. Furthermore, CXCR3 expression by T-cells is induced following T-cell activation and activated T-cells are attracted to sites of inflammation where the IFN-γ inducible chemokines CXCL9, CXCL10 and CXCL11 are secreted.

Mast cells: on their surface express several receptors for chemokines: CCR1, CCR2, CCR3, CCR4, CCR5, CXCR2, and CXCR4. Ligands of these receptors CCL2 and CCL5 play an important role in mast cell recruitment and activation in the lung. There is also evidence that CXCL8 might be inhibitory of mast cells.

Eosinophils: the migration of eosinophils into various tissues involved several chemokines of CC family: CCL11, CCL24, CCL26, CCL5, CCL7, CCL13, and CCL3. Chemokines CCL11 (eotaxin) and CCL5 (RANTES) acts through a specific receptor CCR3 on the surface of eosinophils, and eotaxin plays an essential role in the initial recruitment of eosinophils into the lesion.

Neutrophils: are regulated primarily by CXC chemokines. An example CXCL8 (IL-8) is chemoattractant for neutrophils and also activating their metabolic and degranulation.

Proteins are classified into the chemokine family based on their structural characteristics, not just their ability to attract cells. All chemokines are small, with a molecular mass of between 8 and 10 kDa. They are approximately 20-50% identical to each other; that is, they share gene sequence and amino acid sequence homology. They all also possess conserved amino acids that are important for creating their 3-dimensional or tertiary structure, such as (in most cases) four cysteines that interact with each other in pairs to create a Greek key shape that is a characteristic of chemokines. Intramolecular disulfide bonds typically join the first to third, and the second to fourth cysteine residues, numbered as they appear in the protein sequence of the chemokine. Typical chemokine proteins are produced as pro-peptides, beginning with a signal peptide of approximately 20 amino acids that gets cleaved from the active (mature) portion of the molecule during the process of its secretion from the cell. The first two cysteines, in a chemokine, are situated close together near the N-terminal end of the mature protein, with the third cysteine residing in the center of the molecule and the fourth close to the C-terminal end. A loop of approximately ten amino acids follows the first two cysteines and is known as the N-loop. This is followed by a single-turn helix, called a $3_{10}$-helix, three β-strands and a C-terminal α-helix. These helices and strands are connected by turns called 30s, 40s and 50s loops; the third and fourth cysteines are located in the 30s and 50s loops.

Members of the chemokine family are divided into four groups depending on the spacing of their first two cysteine residues. Thus the nomenclature for chemokines is, e.g.: CCL1 for the ligand 1 of the CC-family of chemokines, and CCR1 for its respective receptor.

CC chemokines. The CC chemokine (or β-chemokine) proteins have two adjacent cysteines (amino acids), near their amino terminus. There have been at least 27 distinct members of this subgroup reported for mammals, called CC chemokine ligands (CCL)-1 to -28; CCL10 is the same as CCL9. Chemokines of this subfamily usually contain four cysteines (C4-CC chemokines), but a small number of CC chemokines possess six cysteines (C6-CC chemokines). C6-CC chemokines include CCL1, CCL15, CCL21, CCL23 and CCL28. CC chemokines induce the migration of monocytes and other cell types such as NK cells and dendritic cells. Examples of CC chemokine include monocyte chemoattractant protein-1 (MCP-1 or CCL2) which induces monocytes to leave the bloodstream and enter the surrounding tissue to become tissue macrophages. CCL5 (or RANTES) attracts cells such as T cells, eosinophils and basophils that express the receptor CCR5. Increased CCL11 levels in blood plasma are associated with aging (and reduced neurogenesis) in mice and humans.

CXC chemokines. The two N-terminal cysteines of CXC chemokines (or α-chemokines) are separated by one amino acid, represented in this name with an "X". There have been 17 different CXC chemokines described in mammals, that are subdivided into two categories, those with a specific amino acid sequence (or motif) of glutamic acid-leucine-arginine (or ELR for short) immediately before the first cysteine of the CXC motif (ELR-positive), and those without an ELR motif (ELR-negative). ELR-positive CXC chemokines specifically induce the migration of neutrophils, and interact with chemokine receptors CXCR1 and CXCR2. An example of an ELR-positive CXC chemokine is interleukin-8 (IL-8), which induces neutrophils to leave the bloodstream and enter into the surrounding tissue. Other CXC chemokines that lack the ELR motif, such as CXCL13, tend to be chemoattractant for lymphocytes. CXC chemokines bind to CXC chemokine receptors, of which seven have been discovered to date, designated CXCR1-7.

C chemokines. The third group of chemokines is known as the C chemokines (or γ chemokines) and is unlike all other chemokines in that it has only two cysteines; one N-terminal cysteine and one cysteine downstream. Two chemokines have been described for this subgroup and are called XCL1 (lymphotactin-α) and XCL2 (lymphotactin-β).

$CX_3C$ chemokines. A fourth group has also been discovered and members have three amino acids between the two cysteines and is termed $CX_3C$ chemokine (or d-chemokines). The only $CX_3C$ chemokine discovered to date is called fractalkine (or $CX_3CL1$). It is both secreted and tethered to the surface of the cell that expresses it, thereby serving as both a chemoattractant and as an adhesion molecule.

Chemokine receptors are G protein-coupled receptors containing 7 transmembrane domains that are found on the surface of leukocytes. Approximately 19 different chemokine receptors have been characterized to date, which are divided into four families depending on the type of chemokine they bind; CXCR that bind CXC chemokines, CCR that bind CC chemokines, CX3CR1 that binds the sole CX3C chemokine (CX3CL1), and XCR1 that binds the two XC chemokines (XCL1 and XCL2). They share many structural features; they are similar in size (with about 350 amino acids), have a short, acidic N-terminal end, seven helical transmembrane domains with three intracellular and three extracellular hydrophilic loops, and an intracellular C-terminus containing serine and threonine residues important for receptor regulation. The first two extracellular loops of chemokine receptors each has a conserved cysteine residue that allow formation of a disulfide bridge between these loops. G proteins are coupled to the C-terminal end of the chemokine receptor to allow intracellular signaling after receptor activation, while the N-terminal domain of the chemokine receptor determines ligand binding specificity.

Chemokine receptors associate with G-proteins to transmit cell signals following ligand binding. Activation of G proteins, by chemokine receptors, causes the subsequent activation of an enzyme known as phospholipase C (PLC). PLC cleaves a molecule called phosphatidylinositol (4,5)-bisphosphate (PIP2) into two second messenger molecules known as Inositol triphosphate (IP3) and diacylglycerol (DAG) that trigger intracellular signaling events; DAG activates another enzyme called protein kinase C (PKC), and IP3 triggers the release of calcium from intracellular stores. These events promote many signaling cascades (such as the MAP kinase pathway) that generate responses like chemotaxis, degranulation, release of superoxide anions and changes in the avidity of cell adhesion molecules called integrins within the cell harboring the chemokine receptor.

The following listing provides cytokines/chemokines examined in the present study:

| | | | | | |
|---|---|---|---|---|---|
| MIF35 | CCL2 | CCL11 | CXCL11 | CXCL1 | CCL13 |
| CXCL12 | CCL21 | IL16 | CCL22 | CCL19 | CXCL10 |
| CXCL9 | CCL27 | CCL27 | CCL25 | CXCL8 | CX3CL1 |
| | CCL20 | CCL23 | CCL15 | CXCL16 | |

III. IMMUNOTHERAPY AND TREATMENT OF IMMUNOTHERAPEUTIC TOXICITY

A. Immunotherapies

Immunotherapy is defined as the treatment of disease by inducing, enhancing, or suppressing an immune response. Immunotherapies designed to elicit or amplify an immune response are classified as activation immunotherapies, while immunotherapies that reduce or suppress are classified as suppression immunotherapies. Immunomodulatory regimens often have fewer side effects than existing drugs, including less potential for creating resistance when treating microbial disease.

Cancer immunotherapy is an example of an activation immunotherapy. Cell-based immunotherapies are effective for some cancers. Immune effector cells such as lymphocytes, macrophages, dendritic cells, natural killer cells (NK Cell), cytotoxic T lymphocytes (CTL), etc., work together to defend the body against cancer by targeting abnormal antigens expressed on the surface of tumor cells. Therapies such as granulocyte colony-stimulating factor (G-CSF), interferons, imiquimod and cellular membrane fractions from bacteria are licensed for medical use. Others including IL-2, IL-7, IL-12, various chemokines, synthetic cytosine phosphate-guanosine (CpG) oligodeoxynucleotides and glucans are involved in clinical and preclinical studies.

Cancer immunotherapy attempts to stimulate the immune system to destroy tumors. A variety of strategies are in use or are undergoing research and testing. Randomized controlled studies in different cancers resulting in significant increase in survival and disease-free period have been reported and its efficacy is enhanced by 20-30% when cell-based immunotherapy is combined with conventional treatment methods.

For example, extraction of G-CSF lymphocytes from the blood and expanding in vitro against a tumor antigen before reinjecting the cells with appropriate stimulatory cytokines can destroy the tumor cells that express the antigen. BCG immunotherapy for early stage (non-invasive) bladder cancer instills attenuated live bacteria into the bladder and is effective in preventing recurrence in up to two thirds of cases. Topical immunotherapy utilizes an immune enhancement cream (imiquimod) which produces interferon, causing the recipient's killer T cells to destroy warts, actinic keratoses, basal cell cancer, vaginal intraepithelial neoplasia, squamous cell cancer, cutaneous lymphoma, and superficial malignant melanoma. Injection immunotherapy ("intralesional" or "intratumoral") uses mumps, candida, the HPV vaccine or trichophytin antigen injections to treat warts (HPV-induced tumors). Adoptive cell transfer has been tested on lung and other cancers.

Dendritic cells can be stimulated to activate a cytotoxic response towards an antigen. Dendritic cells, a type of antigen presenting cell, are harvested from the person needing the immunotherapy. These cells are then either pulsed with an antigen or tumor lysate or transfected with a viral vector, causing them to display the antigen. Upon transfusion into the person, these activated cells present the antigen to the effector lymphocytes (CD4+ helper T cells, cytotoxic CD8+ T cells and B cells). This initiates a cytotoxic response against tumor cells expressing the antigen (against which the adaptive response has now been primed). The cancer vaccine Sipuleucel-T is one example of this approach.

Adoptive cell transfer in vitro cultivates autologous, extracted T cells for later transfusion. The T cells may already target tumor cells. Alternatively, they may be genetically engineered to do so. These T cells, referred to as tumor-infiltrating lymphocytes (TIL), are multiplied using high concentrations of Interleukin-2, anti-CD3 and allo-reactive feeder cells. These T cells are then transferred back into the person along with administration of IL-2 to further boost their anti-cancer activity.

Before reinfusion, lymphodepletion of the recipient is required to eliminate regulatory T cells as well as unmodified, endogenous lymphocytes that compete with the transferred cells for homeostatic cytokines. Lymphodepletion can be achieved by total body irradiation. Transferred cells multiplied in vivo and persisted in peripheral blood in many people, sometimes representing levels of 75% of all $CD8^+$ T cells at 6-12 months after infusion. As of 2012, clinical trials for metastatic melanoma were ongoing at multiple sites.

Autologous immune enhancement therapy use a person's own peripheral blood-derived natural killer cells, cytotoxic T lymphocytes and other relevant immune cells are expanded in vitro and then reinfused. The therapy has been tested against Hepatitis C, Chronic fatigue syndrome and HHV6 infection.

Genetically engineered T cells are created by harvesting T cells and then infecting the T cells with a retrovirus that contains a copy of a T cell receptor (TCR) gene that is specialised to recognize tumor antigens. The virus integrates the receptor into the T cells' genome. The cells are expanded non-specifically and/or stimulated. The cells are then reinfused and produce an immune response against the tumor cells. The technique has been tested on refractory stage IV metastatic melanomas and advanced skin cancer.

B. Immunotherapeutic Toxicity and Treatment Considerations

In general, management of irAEs includes the early recognition and the use of immunosuppressive agents, such as steroids or anti-TNF-α, based on the severity of the event. IrAEs. Most toxicities are mild to moderate, involve mainly skin and GI events, while treatment-related deaths are very rare. Furthermore, the incidence and severity of toxicities is, in some cases, dose related.

The onset and outcome of irAEs with seems to vary according to the organs involved and, although most occur within the first 3 months of treatment, there are some specific toxicities reported months after the end of therapy. The majority of irAEs, however, are seen within the first 3 months of therapy, and the majority also resolve within this same time frame. It is evident that dermatologic irAEs appear usually after 2-3 weeks and typically resolve quickly, GI and hepatic irAEs appear after 6-7 weeks, while endocrinopathies can be diagnosed even after 9 weeks and may take some time to resolve, and rarely are be irreversible.

Skin toxicity, such as rash and pruritus, is common. After eliminating other causes, topical and/or oral steroid therapy can be used, with reduction or skipping of one or more immunotherapy dosings if the condition does not resolve. Only for severe events, will high-dose steroid therapy given intravenously, followed by oral steroids on improvement, be used.

GI adverse events such as diarrhea and colitis are at least as common as skin toxicity. Most treatment guidelines include grading and severity assessment, followed by anti-diarrheic diet and hydration and monitor closely until resolution. Treatment with oral budesonide or other moderate dose steroid can be initiated if the condition persists. In serious/severe cases, treatment with high dose steroids is required. If no response is seen in one week, then immunosuppressive therapy with anti-TNF inhibitors (5 mg/kg remicade, infliximab) may be started.

Liver toxicity, while somewhat more rare, is not uncommon. If hepatotoxicity occurs, the patient should be admitted to the hospital for evaluation and close monitoring and immunotherapy stopped until hepatotoxicity is resolved. IV corticosteroids should be started, and if no improvement, an immunosuppressive agent may be added, further supplemented by tacrolimus if needed.

Endocrine toxicity is fairly common advent in patients receiving immunotherapy. Therefore, routine monitoring of thyroid function at least during treatment and close monitoring of other endocrine function tests is now recommended. Abnormalities are usually easily corrected with hormone replacement. Hypophysitis can remain undetected since the symptoms might be vague, such as fatigue, hypotension or myalgias, and may be missed unless the examining clinician is aware of the risk. Management includes hormone replacement, according to hormone dysfunction (thyroxine, testosterone, estradiol, or more commonly steroids, such as hydrocortisone). Endocrinopathies in general can be managed with a short course of high dose steroid treatment, along with appropriate hormone replacement.

Autoimmune neuropathies are rare but do occur, ranging from mild paresthesias to severe neurologic syndromes. If neuropathy is considered to be significant, immunotherapy should be stopped and treatment with oral or IV steroids started. Ocural toxicity is also rare and it includes conjunctivitis or uveitis, which usually respond well to topical steroid treatment.

Other toxicities include pneumonitis (prompt high-dose steroid initiation and close monitoring of symptoms, oxygen needs and radiological findings), renal toxicity (close monitoring of creatinine, steroid administration and immunotherapy interruption until resolution), and somewhat less frequently myocarditis.

IV. IMMUNODETECTION METHODS

In still further embodiments, the present disclosure concerns immunodetection methods for binding, purifying, removing, quantifying and otherwise generally detecting autoantibodies as well as chemokines/cytokines.

Some immunodetection methods include enzyme linked immunosorbent assay (ELISA), radioimmunoassay (RIA), immunoradiometric assay, fluoroimmunoassay, chemiluminescent assay, bioluminescent assay, and Western blot to mention a few. In particular, a competitive assay for the detection and quantitation of auto-antibodies directed to specific viral epitopes in samples also is provided. The steps of various useful immunodetection methods have been described in the scientific literature, such as, e.g., Doolittle and Ben-Zeev (1999), Gulbis and Galand (1993), De Jager et al. (1993), Nakamura et al. (1987) and Wild, D. (2013). In general, the immunobinding methods include obtaining a sample suspected of containing and autoantibody, and contacting the sample with a first antibody in accordance with the present disclosure, as the case may be, under conditions effective to allow the formation of immunocomplexes.

The immunobinding methods also include methods for detecting and quantifying the amount of autoantibodies in a sample and the detection and quantification of any immune complexes formed during the binding process. Here, one would obtain a sample suspected of containing autoantibodies, and contact the sample with an antigen that binds the autoantibodies or components thereof, followed by detecting and quantifying the amount of immune complexes formed under the specific conditions. In terms of antibody detection, the biological sample analyzed may be any sample that is suspected of containing autoantibodies, such as a tissue section or specimen, a homogenized tissue extract, a biological fluid, including blood and serum, or a secretion, such as feces or urine.

Contacting the chosen biological sample with the antigen under effective conditions and for a period of time sufficient to allow the formation of immune complexes (primary immune complexes) is generally a matter of simply adding the antigen composition to the sample and incubating the mixture for a period of time long enough for the antigen to form immune complexes with, i.e., to bind to autoantibodies present. After this time, the sample-antibody composition, such as a tissue section, ELISA plate, dot blot or Western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. Patents concerning the use of such labels include U.S. Pat. Nos. 3,817,837, 3,850,752, 3,939,350, 3,996,345, 4,277,437, 4,275,149 and 4,366,241. Of course, one may find additional advantages through the use of a secondary binding ligand such as a second antibody and/or a biotin/avidin ligand binding arrangement, as is known in the art.

The antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two-step approach. A second binding ligand, such as an antibody that has binding affinity for the antibody, is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

A. ELISAs

Immunoassays, in their most simple and direct sense, are binding assays. Certain preferred immunoassays are the various types of enzyme linked immunosorbent assays (ELISAs) and radioimmunoassays (RIA) known in the art. Immunohistochemical detection using tissue sections is also particularly useful. However, it will be readily appreciated that detection is not limited to such techniques, and western blotting, dot blotting, FACS analyses, and the like may also be used.

In one exemplary ELISA, the antigens are immobilized onto a selected surface exhibiting protein affinity, such as a well in a polystyrene microtiter plate. Then, a test composition suspected of containing the autoantibodies is added to the wells. After binding and washing to remove non-specifically bound immune complexes, the bound autoantibodies may be detected. Detection may be achieved by the addition of an antibody that binds the Fc portion of the autoantibodies and that is linked to a detectable label. This type of ELISA is a simple "sandwich ELISA."

In another exemplary ELISA, the samples suspected of containing the autoantibodies are immobilized onto the well surface and then contacted with antigen. After binding and washing to remove non-specifically bound immune complexes, the bound autoantibodies are detected. Again, the immune complexes may be detected using a second antibody that has binding affinity for the autoantibodies, with the second antibody being linked to a detectable label.

Irrespective of the format employed, ELISAs have certain features in common, such as coating, incubating and binding, washing to remove non-specifically bound species, and detecting the bound immune complexes. These are described below.

In coating a plate with antigen, one will generally incubate the wells of the plate with a solution of the antigen, either overnight or for a specified period of hours. The wells of the plate will then be washed to remove incompletely adsorbed material. Any remaining available surfaces of the wells are then "coated" with a non-specific protein that is antigenically neutral with regard to the test antisera. These include bovine serum albumin (BSA), casein or solutions of milk powder. The coating allows for blocking of non-specific adsorption sites on the immobilizing surface and thus reduces the background caused by non-specific binding of autoantibodies onto the surface.

In ELISAs, it is probably more customary to use a secondary or tertiary detection means rather than a direct procedure. Thus, after binding of an antigen to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, and a secondary binding ligand or antibody in conjunction with a labeled tertiary antibody or a third binding ligand.

"Under conditions effective to allow immune complex (antigen/antibody) formation" means that the conditions preferably include diluting the antigens and/or antibodies with solutions such as BSA, bovine gamma globulin (BGG) or phosphate buffered saline (PBS)/Tween. These added agents also tend to assist in the reduction of nonspecific background.

The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C. or may be overnight at about 4° C. or so.

Following all incubation steps in an ELISA, the contacted surface is washed so as to remove non-complexed material. A preferred washing procedure includes washing with a solution such as PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. Preferably, this will be an enzyme that will generate color development upon incubating with an appropriate chromogenic substrate. Thus, for example, one will desire to contact or incubate the first and second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea, or bromocresol purple, or 2,2'-azino-di-(3-ethyl-benzthiazoline-6-sulfonic acid (ABTS), or $H_2O_2$, in the case of peroxidase as the enzyme label. Quantification is then achieved by measuring the degree of color generated, e.g., using a visible spectra spectrophotometer.

In another embodiment, the present disclosure contemplates the use of competitive formats. This is particularly useful in the detection of autoantibodies in sample. In competition-based assays, an unknown amount of analyte or competing antibody is determined by its ability to displace a known amount of labeled antibody or analyte. Thus, the quantifiable loss of a signal is an indication of the amount of unknown antibody or analyte in a sample.

Here, the inventors propose the use of labeled autoantibodies to determine the amount of autoantibodies in a sample. The basic format would include contacting a known amount of autoantibodies (linked to a detectable label) with the antigen. The antigen is preferably attached to a support. After binding of the labeled monoclonal antibody to the support, the sample is added and incubated under conditions permitting any unlabeled autoantibodies in the sample to compete with, and hence displace, the labeled monoclonal antibody. By measuring either the lost label or the label remaining (and subtracting that from the original amount of bound label), one can determine how much non-labeled antibody is bound to the support, and thus how much autoantibody was present in the sample.

B. Western Blot

The Western blot (alternatively, protein immunoblot) is an analytical technique used to detect specific proteins in a given sample of tissue homogenate or extract. It uses gel electrophoresis to separate native or denatured proteins by the length of the polypeptide (denaturing conditions) or by the 3-D structure of the protein (native/non-denaturing conditions). The proteins are then transferred to a membrane (typically nitrocellulose or PVDF), where they are probed (detected) using antibodies specific to the target protein.

Samples may be taken from whole tissue or from cell culture. In most cases, solid tissues are first broken down mechanically using a blender (for larger sample volumes), using a homogenizer (smaller volumes), or by sonication. Cells may also be broken open by one of the above mechanical methods. However, it should be noted that bacteria, virus or environmental samples can be the source of protein and thus Western blotting is not restricted to cellular studies only. Assorted detergents, salts, and buffers may be employed to encourage lysis of cells and to solubilize proteins. Protease and phosphatase inhibitors are often added to prevent the digestion of the sample by its own enzymes. Tissue preparation is often done at cold temperatures to avoid protein denaturing.

The proteins of the sample are separated using gel electrophoresis. Separation of proteins may be by isoelectric point (pI), molecular weight, electric charge, or a combination of these factors. The nature of the separation depends on the treatment of the sample and the nature of the gel. This is a very useful way to determine a protein. It is also possible to use a two-dimensional (2-D) gel which spreads the proteins from a single sample out in two dimensions. Proteins are separated according to isoelectric point (pH at which they have neutral net charge) in the first dimension, and according to their molecular weight in the second dimension.

In order to make the proteins accessible to antibody detection, they are moved from within the gel onto a membrane made of nitrocellulose or polyvinylidene difluoride (PVDF). The membrane is placed on top of the gel, and a stack of filter papers placed on top of that. The entire stack is placed in a buffer solution which moves up the paper by capillary action, bringing the proteins with it. Another method for transferring the proteins is called electroblotting and uses an electric current to pull proteins from the gel into the PVDF or nitrocellulose membrane. The proteins move from within the gel onto the membrane while maintaining the organization they had within the gel. As a result of this blotting process, the proteins are exposed on a thin surface layer for detection (see below). Both varieties of membrane are chosen for their non-specific protein binding properties (i.e., binds all proteins equally well). Protein binding is based upon hydrophobic interactions, as well as charged interactions between the membrane and protein. Nitrocellulose membranes are cheaper than PVDF but are far more fragile and do not stand up well to repeated probing. The uniformity and overall effectiveness of transfer of protein from the gel to the membrane can be checked by staining the membrane with Coomassie Brilliant Blue or Ponceau S dyes. Once transferred, proteins are detected using labeled primary antibodies, or unlabeled primary antibodies followed by indirect detection using labeled protein A or secondary labeled antibodies binding to the Fc region of the primary antibodies.

C. Immunodetection Kits

In still further embodiments, the present disclosure concerns immunodetection kits for use with the immunodetection methods described above. The immunodetection kits will thus comprise, in suitable container means, one or more antibodies that bind to autoantigens and/or chemokines/cytokines, and optionally an immunodetection reagent.

In certain embodiments, the antibody may be pre-bound to a solid support, such as a column matrix and/or well of a microtiter plate. The immunodetection reagents of the kit may take any one of a variety of forms, including those detectable labels that are associated with or linked to the given antibody. Detectable labels that are associated with or attached to a secondary binding ligand are also contemplated. Exemplary secondary ligands are those secondary antibodies that have binding affinity for the first antibody.

Further suitable immunodetection reagents for use in the present kits include the two-component reagent that comprises a secondary antibody that has binding affinity for the first antibody, along with a third antibody that has binding affinity for the second antibody, the third antibody being linked to a detectable label. As noted above, a number of exemplary labels are known in the art and all such labels may be employed in connection with the present disclosure.

The kits may further comprise a suitably aliquoted composition of the antigen or antigens, whether labeled or unlabeled, as may be used to prepare a standard curve for a detection assay. The kits may contain antibody-label conjugates either in fully conjugated form, in the form of intermediates, or as separate moieties to be conjugated by the user of the kit. The components of the kits may be packaged either in aqueous media or in lyophilized form.

The container means of the kits will generally include at least one vial, test tube, flask, bottle, syringe or other container means, into which the antibody may be placed, or preferably, suitably aliquoted. The kits of the present disclosure will also typically include a means for containing the antibody, antigen, and any other reagent containers in close confinement for commercial sale. Such containers may include injection or blow-molded plastic containers into which the desired vials are retained.

In addition, there are multiple commercialized multiplex assays that are used in clinical laboratories to evaluate for autoantigens and/or allergens. These formats include spotted microarrays, bead/particle-based assays (e.g., Luminex, as employed by the inventors for the work reported herein), line probe (e.g., Innogenetics), and cartridges (Hitachi Optigen).

V. EXAMPLES

The following examples are included to demonstrate preferred embodiments. It should be appreciated by those of skill in the art that the techniques disclosed in the examples that follow represent techniques discovered by the inventors to function well in the practice of embodiments, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1—Materials and Methods

Subject recruitment. This study was approved by the UT Southwestern Institutional Review Board (IRB #STU 082015-053). All patients provided informed consent. The inventors enrolled patients with cancer receiving immune checkpoint inhibitor therapy, as well as healthy controls. Potential subjects were identified, screened, and recruited through the following mechanisms: (i) direct contact between study team members and clinic personnel to remind staff of the study availability, answer questions, and solicit support through patient referrals; (ii) systemic data extraction of new immune checkpoint inhibitor orders through the ClinDen Data Extraction system; and (iii) weekly notifications through the EPIC electronic medical record, through which all referrals for new immunotherapy orders were routed to the study team. Key eligibility criteria included age≥18 years; no prior treatment with immune checkpoint inhibitor-based therapy (PD1, PDL1, CTLA4 inhibitors); planned for but not yet initiated immune checkpoint inhibitor-based therapy; and willingness to provide required blood samples and clinical follow-up. For enrolled subjects, the following data were captured: age; sex; race/ethnicity; cancer type and stage; type and dates of immune checkpoint inhibitor therapy; and prior therapies.

Data and sample collection. Peripheral blood samples were collected from patients at baseline, after 1 treatment cycle (either 2 weeks or 3 weeks) and at 6 weeks. Two samples were collected from healthy controls approximately 2-3 weeks apart. Blood samples were centrifuged at approximately 3000 rpm at 4° C. for 15 minutes to obtain serum. Research coordinators collected clinical data, including demographics, cancer type, treatment type, and irAEs). Review of all cases for presence, timing, and type of irAE was performed independently by two clinician co-authors experienced in the administration of immune checkpoint inhibitor therapy (S.A.K. and D.E.G.). Any differences between these assessments were discussed with and adjudicated by the entire study team.

Cytokine/chemokine analysis. Monitoring of cytokine and chemokine was performed using Bio-Plex Pro Human Chemokine 40-plex Panel (Bio-Rad Laboratories, Hercules, California) according to the manufacturer's instructions using a Luminex 200 System. The list of cytokines and chemokines are provided in Supplemental Table 1. Bio-Plex Manager™ 6.1 software was used for data analysis. Concentrations of cytokines and chemokines (pg/mL) were determined on the basis of the fit of a standard curve for mean fluorescence intensity versus pg/ml.

IgG levels. Total serum IgG levels were measured using commercial human Total IgG ELISA kit (Invitrogen, California) as per the manufacturer protocol. Serum samples were serially diluted 1:500,000 and concentration of total IgG was determined on the basis of standard curve using 8-point standard curve (ng/ml). All the values were converted to clinically relevant measurements of mg/dL.

Statistical analysis. The Chi-square test or Fisher's exact test was used to compare baseline versus post-treatment levels of cytokines/chemokines and total IgG. Results were expressed as the mean±standard error (SE). To determine the association between biomarker data and development of irAEs, the inventors used Student's t test, the Mann-Whitney U test, 1-way parametric ANOVA and Tukey post hoc comparison or Dunn's multiple comparison test when applicable. For toxicity analyses, because irAEs may occur throughout the course of treatment with immune checkpoint inhibitors, patients were considered not to have developed irAEs only if they had been followed for at least 3 months. In sensitivity analyses, the inventors used a minimum follow-up period of 6 months. Statistical analyses were performed using GraphPad Prism Software (GraphPad Software Inc, La Jolla, CA, USA). For all statistical analysis, the level of significance was set at P<0.05.

Example 2—Results

Patients. The inventors enrolled a total of 78 subjects, including 65 patients with cancer receiving immune checkpoint inhibitor therapy and 13 healthy controls. Baseline demographic, tumor, and treatment data are listed in Table 1. Sixty-four patients received anti-PD1/PDL1 therapy alone (n=59) or in combination with anti-CTLA4 therapy (n=5). Only one patient in our cohort received anti-CTLA4 monotherapy. Among the 65 patients receiving immune checkpoint inhibitor therapy, they collected baseline samples in 47 cases, samples at 2-3 weeks in 38 cases, and samples at 6 weeks in 40 cases.

Cytokine/chemokine levels. Among the 40 cytokines/chemokines assessed, levels of two cytokines (GM-CSF and CXCL5) were below detection levels and were therefore eliminated from analysis. Hierarchical clustering of 38 cytokines and chemokines clearly separated healthy controls from cancer patients as shown in the heatmap in FIG. 1A. Specifically, 14 cytokines were significantly up-regulated in cancer patients at baseline compared to healthy controls. Cytokine levels were stable in healthy controls with no significant differences between the two time-points. However, the inventors observed significant changes in cytokine levels in patients after initiation of immunotherapy. At the 2-week time-point, there were significant increases in serum levels of CXCL9, CXCL10, CXCL11 and CXCL13 (FIG. 1B). At 6 weeks post-treatment, serum levels of CXCL9, CXCL10, CXCL11, CXCL13, IL-10 and CCL26 were significantly up-regulated in patient cohort (FIG. 1C).

Among a total of 47 patients profiled for cytokines/chemokines, 16 patients developed irAEs on checkpoint inhibitor therapy. These autoimmune toxicities included pneumonitis, endocrinopathies, dermatitis, arthritis and encephalitis (Table 1). The inventors divided the patient cohort into two groups based on whether they developed any immune-related adverse events. In the no-irAE group (n=31), at baseline 12 cytokines were significantly up-regulated when compared to healthy controls (FIG. 1D). The irAE group (n=16) had significantly elevated levels of 5 cytokines IL-6, CXCL2, CCL20, CXCL8 and CCL23 compared to healthy controls (FIG. 1E).

Figure 2:
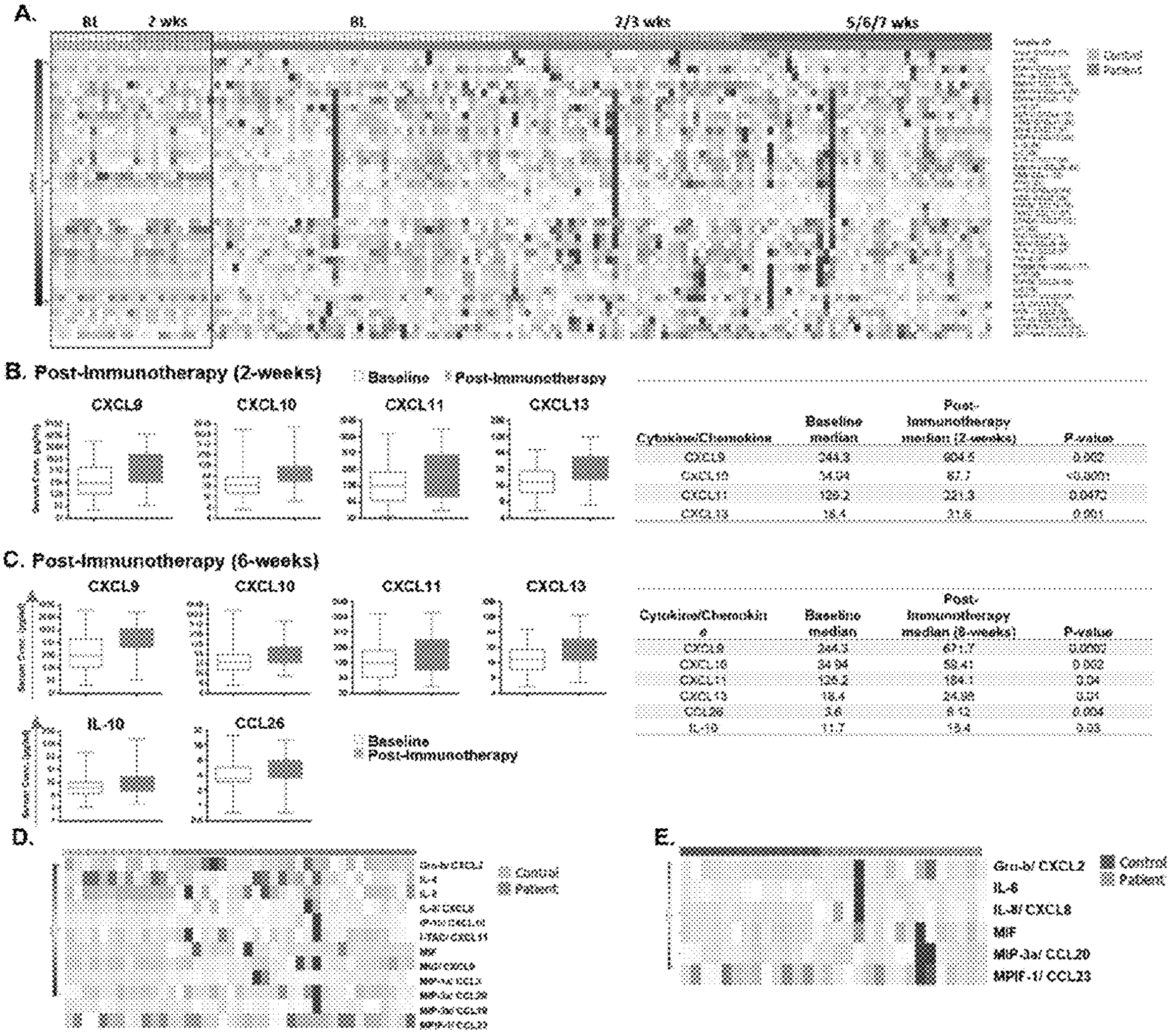
FIGS. 2A-E.

Notably, patients who developed irAEs had lower baseline serum levels of several cytokines/chemokines compared to patients who did not develop irAEs (FIG. 2A). In particular, significantly lower levels of CXCL9, CXCL10, CXCL11 and CCL19 at baseline were observed in the irAE group (FIG. 2B). Conversely, the -fold increase in cytokines/chemokines at 2-3 weeks and at 6 weeks (particularly for CXCL9 and CXCL10) was significantly greater in the irAE group (FIG. 2C).

Total IgG levels. As a surrogate marker of immune status, the inventors determined total IgG levels using a commercial ELISA assay. There were no significant changes in levels of serum total IgG at 2 weeks or 6 weeks post immunotherapy in any patient group. However, patients who developed irAEs had significantly reduced levels of serum IgG levels at baseline compared to patients who did not develop irAEs (FIG. 2D). This observation echoed the inventors' cytokine data, which showed reduced baseline levels of cytokines and chemokines patients developing irAEs.

Figure 3:
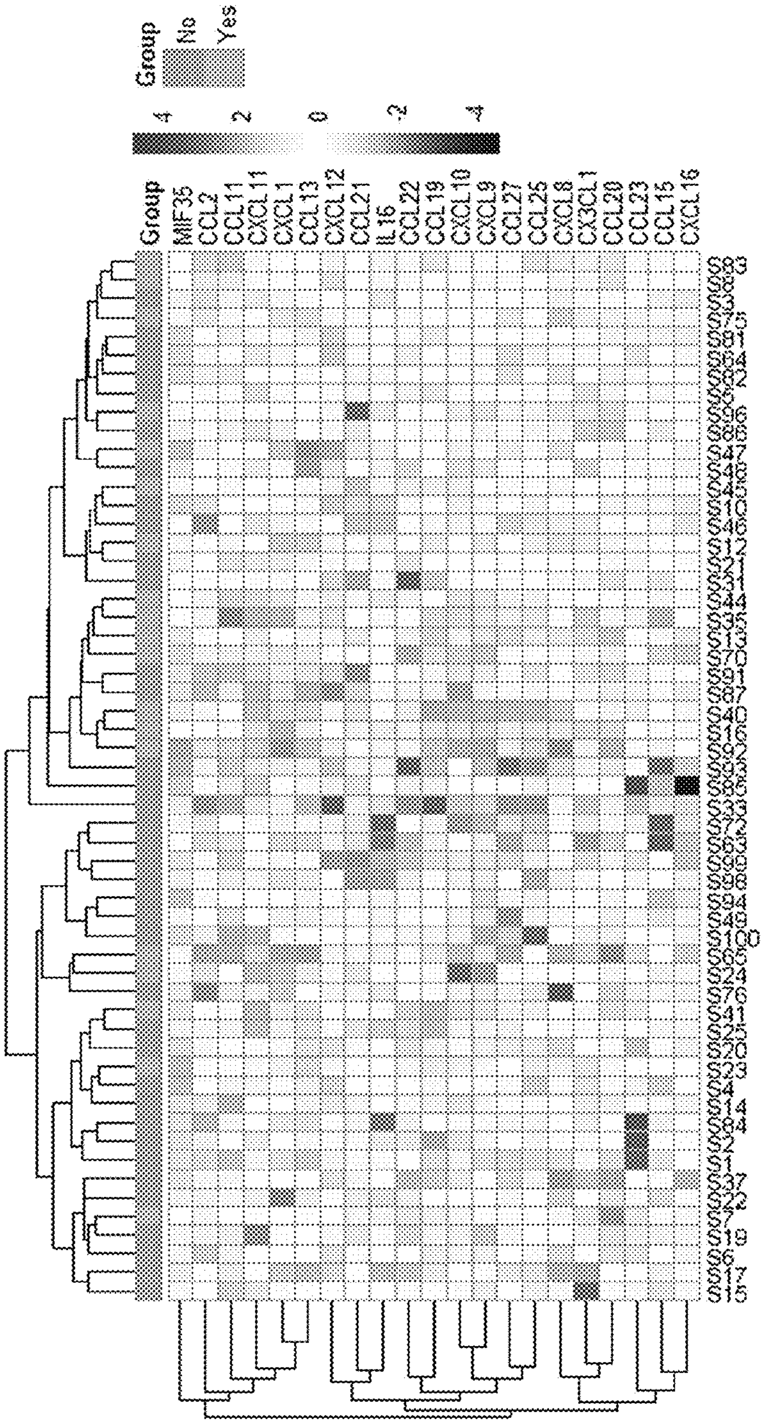
FIG. 3. Heatmap of 21 cytokines clustered the samples into two big groups as shown by the column, most toxicity group (Yes) has relatively low cytokine levels at baseline as compared to the non-toxicity group (No).
Figure 5:
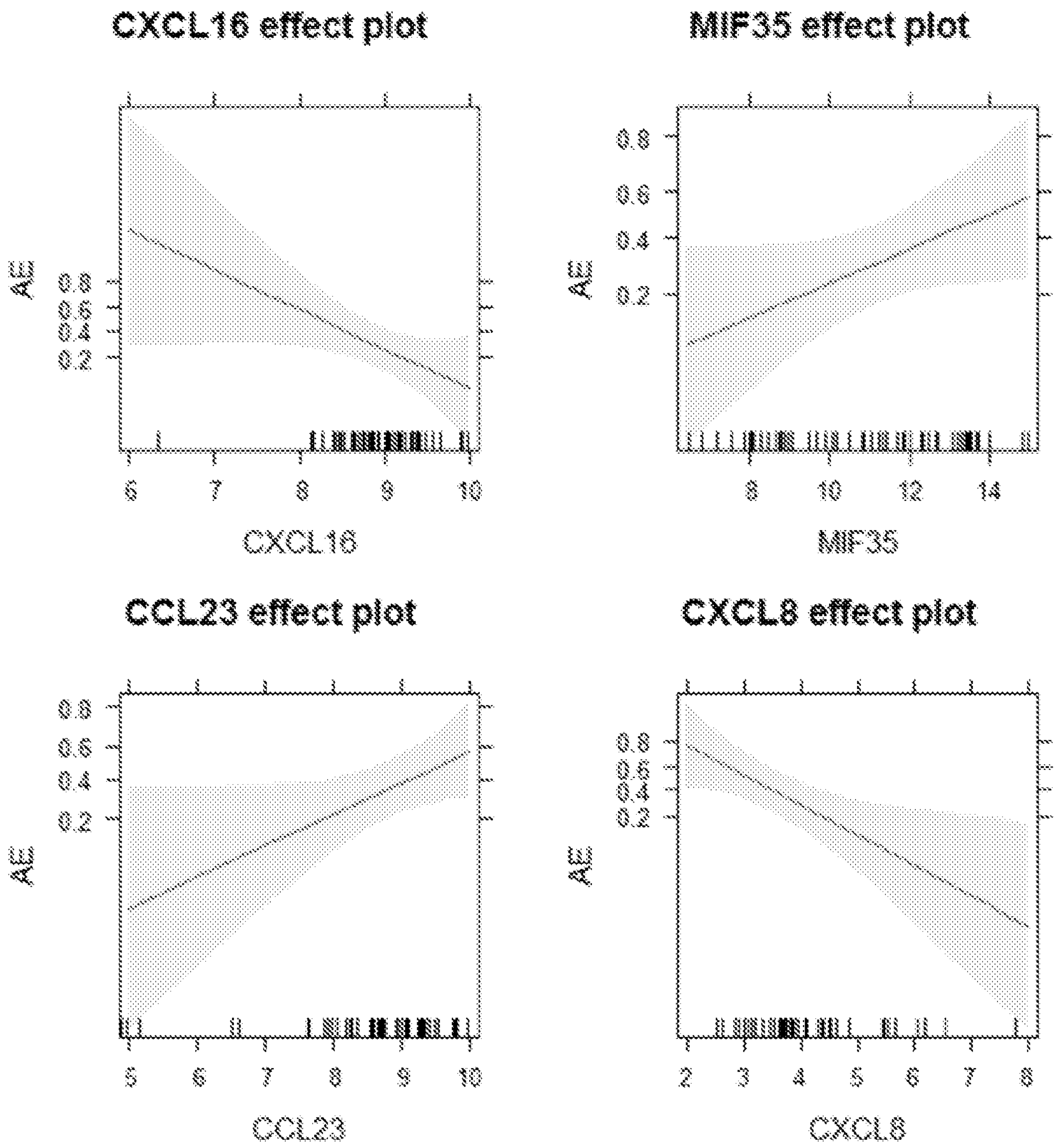
FIG. 5. Four important predictors of possible AE occurrence. Effect plots for each cytokine shown that lower or higher baseline patients are more likely to develop toxicity. s axis log 2 transformed cytokine level; y axis probability of developing AE.
Figure 6:
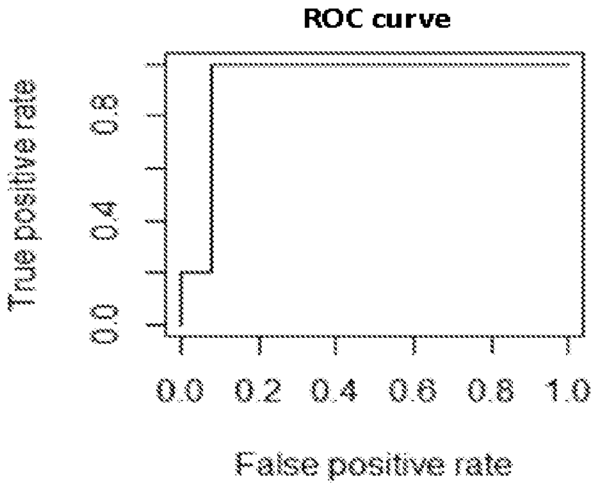
FIG. 6. Random partition of the patients in 38 (14 with AE) as a training set and 18 (5 with AE) as test set to build and assess prediction model.

FIG. 3 shows heatmap of 21 cytokines that clustered the samples into two big groups. As you can appreciate in the heatmap, most patients that developed toxicity displayed lower cytokine levels at baseline before the initiation of checkpoint blockade when compared to patients that did not develop toxicities. Logistic regression model analysis of 21 cytokines identified CXCL8, MIF35, CXCL16 and CCL23 as important predictors of development of toxicity as shown in FIG. 4. The inventors generated effect plots of these four cytokines to predict the occurrence of autoimmune toxicities (FIG. 5). The effect plots revealed that the patients with lower baseline levels of CXCL8 are more likely to develop irAEs whereas patients with higher baseline levels of CXCL16 have higher probability to develop irAEs. The inventors generated ROC curves also known as relative operating characteristic curve based by plotting true positive rate (TPR) against false positive rate (FPR). The accuracy of the four cytokines was used to see how well it can separate patients tested into those with and without immune toxicities. The accuracy of the test is measured by the area under the ROC curve. An area of 1 represents a perfect test and an area of 0.5 represents a worthless test. The accuracy of the current model using four cytokines is 0.8224 as depicted in the ROC curves. The values for sensitivity, specificity, positive and negative prediction are 0.92, 0.6, 0.86 and 0.75 respectively as shown in FIG. 6.

Figure 7:
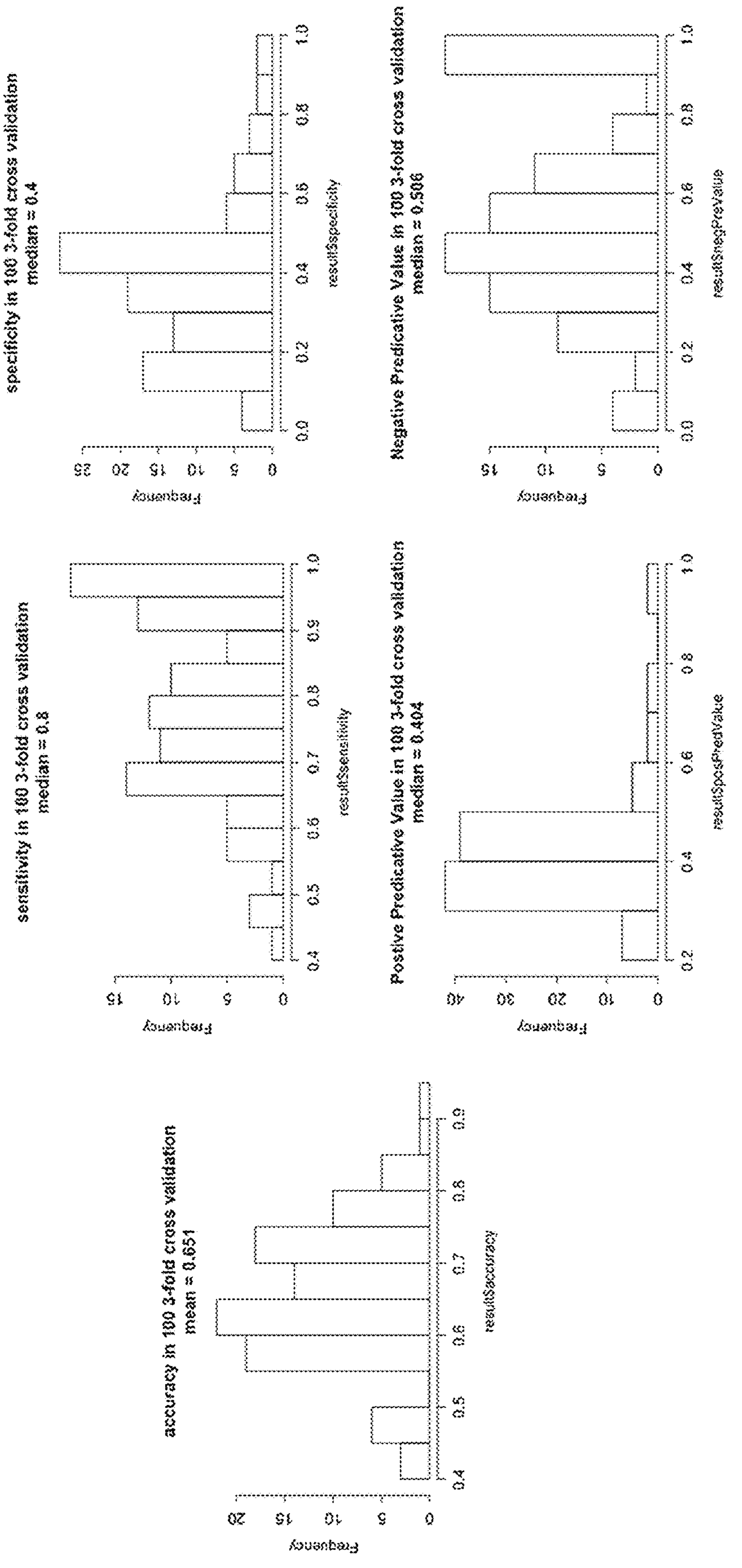
FIG. 7. 100-times 3-fold cross validation to test the stability of the prediction model. 56 patients were randomly separated into training and test sets for 100 time. The accuracy of each partition shows that the majority of the 100-times test yields and accuracy of >0.6. With increasing sample size, a more stable and accurate model for AE is predicted.
Figure 8:
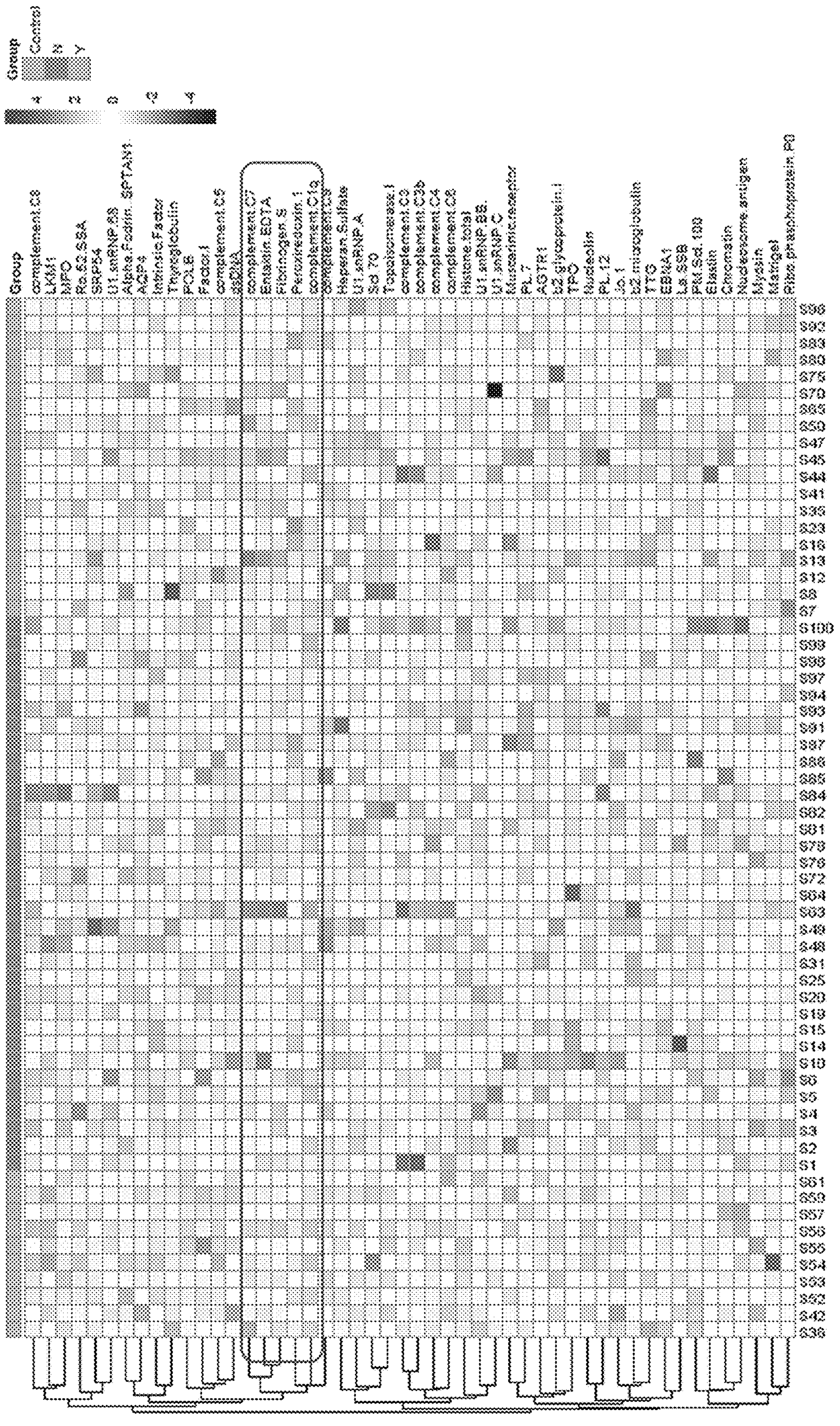
FIG. 8. Measurement of fifty auto-antibodies across healthy control, patients without AE and patients with AE at baseline level. Stringent cutoff was used to keep only the auto-antibodies with SNR>3 in all samples. Auto-antibodies in the rectangle labeled appear higher in patients who developed toxicity.

The inventors then performed statistical analysis using 100×3-fold cross validation to test the stability of the prediction model. They randomly separated 56 patients into training and testing sets for 100 times. FIG. 7 shows the accuracy for each partition and the majority of 100 times test yield an accuracy>0.6 for prediction of autoimmune toxicities. The median values for sensitivity, specificity, positive prediction and negative prediction in 100×3-fold cross validation are 08, 0.4, 0.4 and 0.5 respectively.

Figure 9:
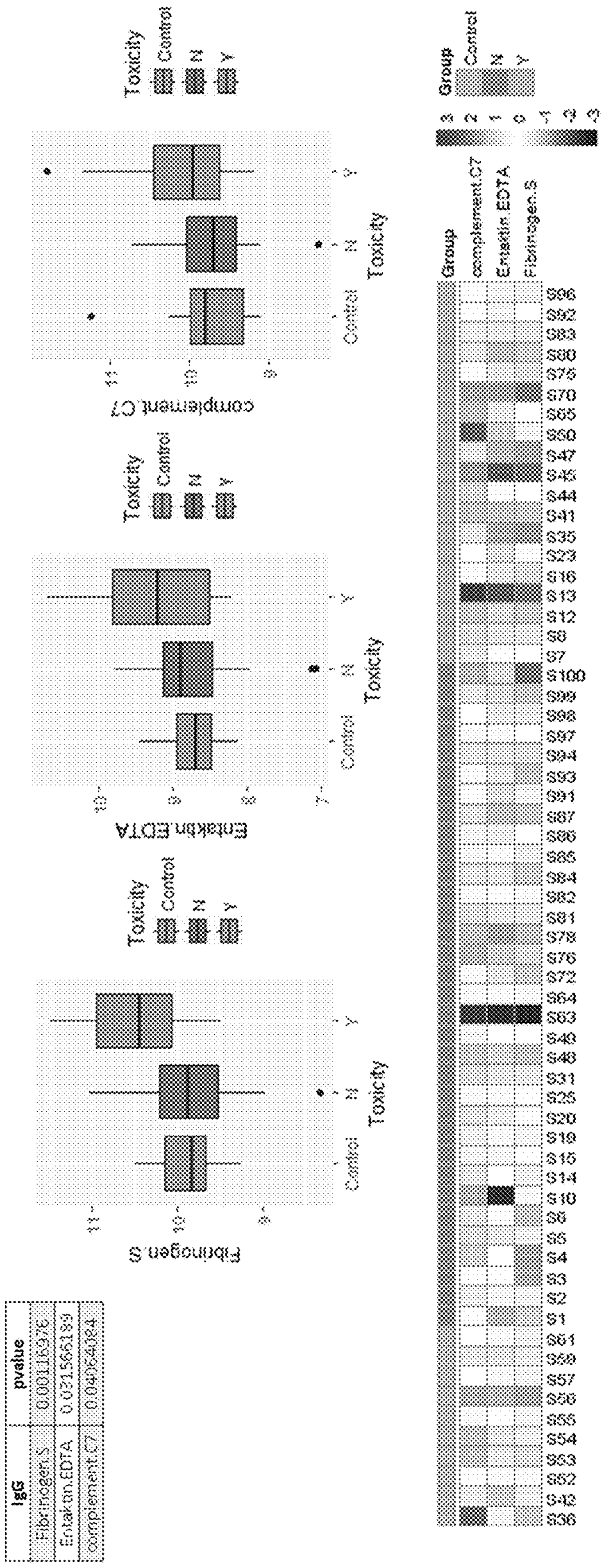
FIG. 9. ANOVA test to identify autoantibodies with significant changes. Patients with AE have shown significantly elevated levels of autoantibodies at baseline level as compared with patients without AE or healthy control. Of these, blood coagulation protein fibrinogen has been shown to promote autoimmunity and demyelination via chemokine release and antigen presentation.
Figure 10:
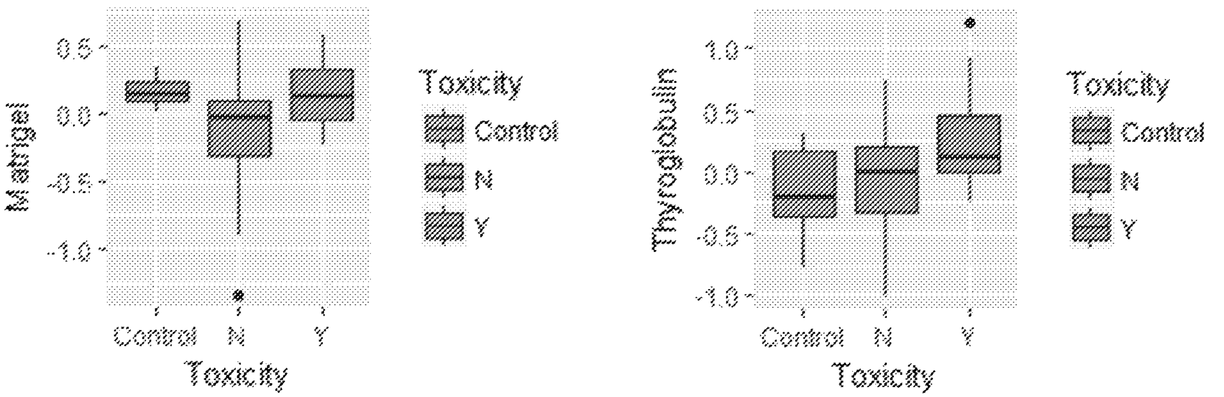
FIG. 10. Two out of 50 IgG are altered significantly two weeks post-treatment in toxicity group vs non-toxicity group Following graphs showing log transformed fold change in each group of patients two weeks versus baseline.
Figure 11:
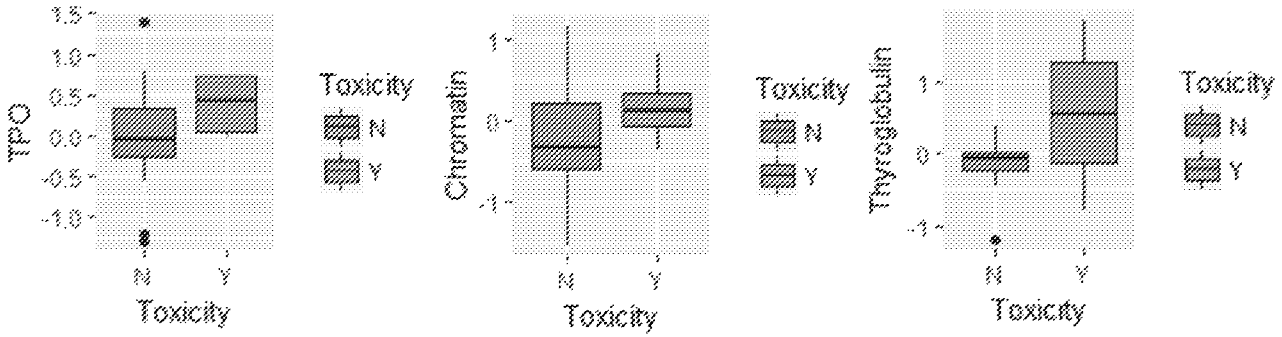
FIG. 11. Three out of 50 IgG altered significantly six weeks post-treatment in toxicity group versus non-toxicity group. Graphs show log transformed-fold change in each group of patients two weeks versus baseline.
Figure 12:
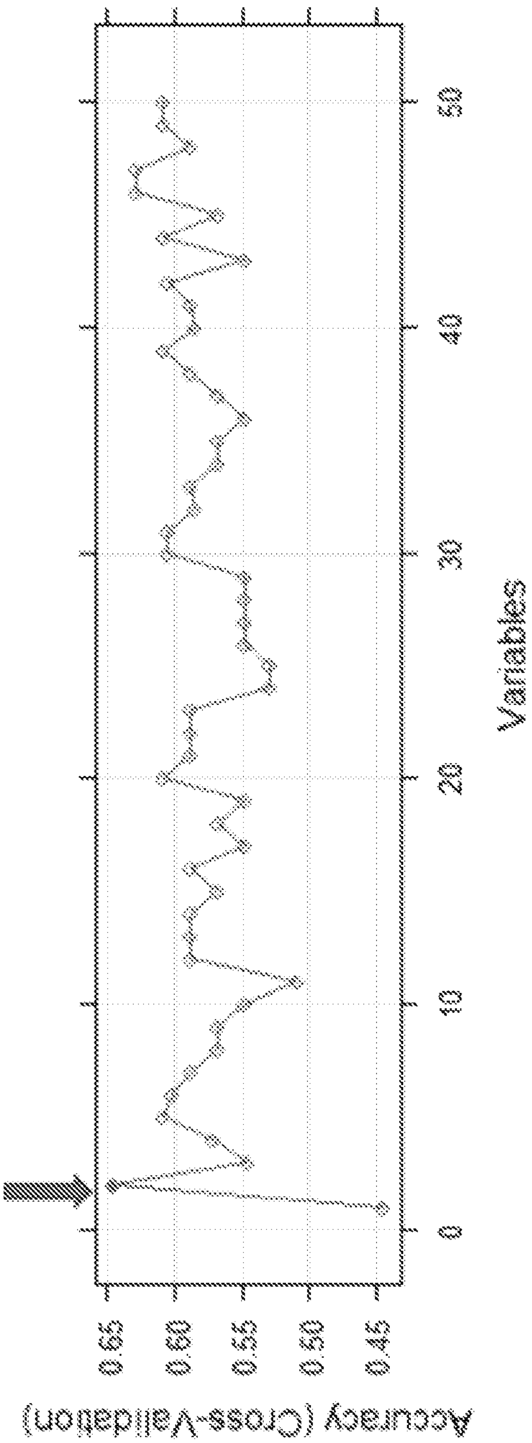
FIGS. 12-13. Random Forest Model in Caret package to select important IgG that could predict toxicity at baseline level. Based on cross-validation, the baseline level of two IgGa can predict toxicity at 65% accuracy which, considering the toxicity rate, is about 19/51 (37%). Even with less robust models, Entaktin and Fibrinogen are consistently different between toxicity and non-toxicity groups both in multivariate and univariate analysis. Data developed from a set of 32 patients without toxicity and 19 patients who developed toxicity.
Figure 13:
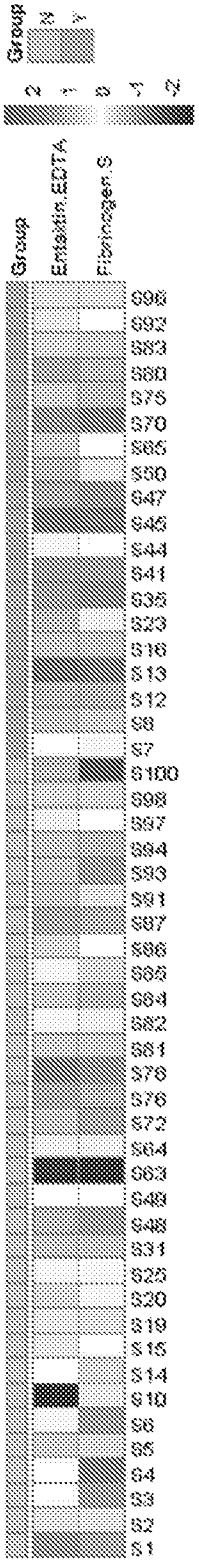

Releasing the brakes off the immune system via PD-1 and CTLA-4 immunoregulatory pathways would result in mounting a strong host immune response. This led us to hypothesize that there would be significant modulation in humoral immune response in response to immunoregulatory therapy that would potentially reveal serum biomarkers associated with toxicity. In order to address this, the inventors performed a detailed analysis of modulations in a patient's humoral immune system during immunotherapy using custom autoantigen array with 124 different antigens. Autoantibody titers in healthy controls showed a heterogenous profile, however the levels remained stable when tested again after two weeks. The inventors then evaluated the humoral autoimmune responses at baseline, 2-week and 6-week post immunoregulatory therapy in our cancer patient cohort (n=65) treated with immune checkpoint blockade. Cancer patients at baseline level showed extensive variability in humoral immune responses. FIG. 9 represents a heatmap of 50 autoantibodies with stringent cutoff of SNR>3 across healthy control and patients with and without irAEs at baseline level. The inventors performed the ANOVA test to identify autoantibodies that are significantly different in patients who developed toxicities versus patients with no toxicities. Fibrinogen, entactin.EDTA and complement C7 were significantly upregulated in the toxicity group at baseline levels as shown in FIG. 9. These autoantibodies have been associated with demyelination, inflammatory arthritis and SLE. Comparative analysis of autoantibodies at two-week post treatment revealed two cytokines, Matrigel and thyroglobulin, significantly different in toxicity group versus non-toxicity group (FIG. 10). At 6-week post treatment, three cytokines including TPO, chromatin and thyroglobulin were significantly upregulated in toxicity group versus no-toxicity group as shown in FIG. 11. The inventors used Random Forest Model in Caret package to select important IgG that could predict toxicity at baseline level. Based on cross validation, baseline levels of Entaktin and Fibrinogen together can predict the toxicity at 65% accuracy (FIG. 12). Entaktin and Fibrinogen were differentially regulated in toxicity versus no-toxicity groups both in multivariate and univariate analysis as shown in the heatmap in FIG. 13.

Example 3—Discussion

Despite extensive preclinical research, several drug approvals in multiple cancer types, and hundreds of ongoing clinical trials in cancer immunotherapy, immune-related adverse events remain a largely understudied and poorly understood phenomenon. Complicating the study of these autoimmune toxicities is their diverse and unpredictable presentation. To date, apart from the hypothetical concern that pre-existing autoimmune disease may be exacerbated by immune checkpoint inhibitor therapy (resulting in exclusion of these patients from most immunotherapy clinical trials (Khan et al., 2016; 2018). There have been no clear demographic or clinical factors associated with these events. Furthermore, in contrast to classic toxicities of conventional chemotherapy such as myelosuppression, irAEs may occur at any point in therapy and rarely have a discrete laboratory test to aid in diagnosis. Recognizing that irAEs are more likely to reflect host rather than tumor biology, in this study the inventors focused on markers of systemic immune status. The inventors found that patients with lower levels of pre-treatment immune markers (immunoglobulins and cytokines) experienced greater increases in these parameters after treatment initiation, and also had greater risk of irAEs.

These findings echo earlier observations that autoimmune diseases may occur at greater rates in chronically immunosuppressed populations. A classic example is the association of HIV/AIDS with autoimmunity (Zandman-Goddard and Shoenfeld, 2002). In this population, the frequency of reported rheumatological conditions ranges up to 60%. Specific reported diseases include systemic lupus erythematosus, anti-phospholipid syndrome, vasculitis, immune thrombocytopenic purpura, polymyositis, and others. These patients also have a variety of autoantibodies, among them anti-DNA, anti-cardiolipin, anti-thyroglobulin, and anti-myosin. Coupled with these epidemiologic findings, the current study suggests that immune dysregulation may heighten risk of autoimmune events, specifically irAEs in patients treated with immune checkpoint inhibitors.

In the present study, patterns of CXCL 9, 10, 11, and 19 levels had the strongest association with irAEs. All were lower at baseline, and CXCL 9 and 10 had particularly large increases after therapy started. These interferon-gamma inducible small cytokines are chemotactic for activated T cells. They have also been implicated in a variety of autoimmune conditions, including thyroiditis, type 1 diabetes mellitus, and Addison's disease, inflammatory bowel disease, and systemic sclerosis (Rotondi et al., 2007; Marshall et al., 2017). Cytokine levels have been evaluated in earlier studies of immune checkpoint inhibitors, with primary focus on anti-tumor efficacy (Yamazaki et al., 2017). One study of neoadjuvant ipilimumab for melanoma found that baseline interleukin-17 was associated with development of diarrhea/colitis (Tarhini et al., 2015). That the inventors identified a different pattern of cytokines in the present study may reflect the predominance of anti-PD1/PDL1 therapy and low rates of gastrointestinal toxicity (which is more commonly associated with anti-CTLA4 treatment).

The inventors' observation of baseline elevated cytokine/chemokine levels among individuals with cancer compared to healthy controls echoes findings from earlier studies. In colorectal cancer, serum cytokine alterations occur in a stage-dependent fashion (Kantola et al., 2012). In pancreatic cancer, levels of IL-6, -8, -10 and TNFα are higher than in healthy controls (Blogowski et al., 2014). Whether these profiles represent a chronic inflammatory state predisposing to cancer, or a reaction to the malignancy, remains unclear.

While research into irAEs remains a nascent field, for some conditions predictive biomarkers are emerging. Among patients treated with pembrolizumab, anti-thyroid antibodies were present in 80% of patients who developed thyroid dysfunction, compared with 8% who did not ($P<0.0001$) (Osorio et al., 2017). Although this observation suggests that PD-1 biology modulates humoral immunity, it is not realistic to expect that discrete and tissue-specific autoantibodies will be identified for most irAEs. Indeed, many autoimmune disorders, particularly those involving the lungs, do not have serologic correlates. For those conditions with associated autoantibodies, such as systemic lupus erythematosis, the functional significance of the antibody often remains unclear.

Limitations of this study include the single-center setting, the predominance of a single cancer type (lung cancer, which reflects the clinical focus of the authors), and the inherent challenges of clinically diagnosing and characterizing many irAEs. Additionally, relatively small patient numbers preclude analysis according to type of immunotherapy, or type and severity of irAE. Strengths include the availability of serial specimens, the requirement that patients have at least three months follow-up before being considered without irAE, and the use of rigorous statistical methods to account for repeated testing.

In conclusion, among cancer patients treated with immune checkpoint inhibitors, irAEs may be more common among those exhibiting immune dysregulation. Specifically, lower baseline levels and greater post-treatment increases in cytokines associated with T cell activation and autoimmune disease were observed in irAE cases. Biomarkers for the prediction and tracking of autoimmune toxicity in this population could serve to customize therapy, tailor monitoring, and even expand the use of checkpoint inhibitors to groups in which they are currently avoided.

TABLE 1

Characteristics of Patients, Treatement and Autoimmune Toxicity

| Type of Cancer | | # of Cases |
|---|---|---|
| Lung | | 53 |
| Kidney | | 5 |
| Melanoma | | 4 |
| Head/Neck | | 1 |
| Liver | | 1 |
| Bladder | | 1 |
| **Treatment** | **Number of patients** | **Immune Toxicity** |
| PD1 | 49 | 17 |
| PDL1 | 10 | 3 |
| CTLA-4 | 1 | 1 |
| PD1 + CTLA-4 | 5 | 3 |
| **Immune Toxicity** | | **# of Patients** |
| Pneumonitis | | 10 |
| Arthritis | | 2 |

TABLE 1-continued

| Characteristics of Patients, Treatement and Autoimmune Toxicity | |
|---|---|
| Dermatitis | 2 |
| Hypophysitis | 2 |
| Thyroid | 3 |
| Neuro (encephalitis) | 1 |
| *"Complex" | 3 |

Supplemental Table 1 - Cytokines and Chemokines Included in Analysis

| Cytokines and Chemokines | | |
|---|---|---|
| 6Ckine/CCL21 | ENA-78/CXCL5 | IFN-y |
| CTACK/CCL27 | BCA-1/CXCL13 | IL-1b |
| Eotaxin/CCL11 | Fractalkine/CX3CL1 | IL-2 |
| Eotaxin-2/CCL24 | GCP-2/CXCL6 | IL-4 |
| Eotaxin-3/CCL26 | Gro-a/CXCL1 | IL-6 |
| I-309/CCL1 | Gro-b/CXCL2 | IL-10 |
| MCP-1/CCL2 | SCYB16/CXCL16 | IL-16 |
| MCP-2/CCL8 | SDF-1a + b/CXCL12 | GM-CSF |
| MCP-3/CCL7 | IP-10/CXCL10 | MIF |
| MCP-4/CCL13 | I-TAC/CXCL11 | |
| MDC/CCL22 | MIG/CXCL9 | |
| MIP-1a/CCL3 | IL-8/CXCL8 | |
| MIP-1d/CCL15 | | |
| MIP-3a/CCL20 | | |
| MIP-3b/CCL19 | | |
| MPIF-1/CCL23 | | |

Example 4—Single Cell RNA Sequencing

Comprehensive Chromium Single Cell Immune Profiling assay (10× Genomics) which includes high resolution gene expression profiling and paired (TCR α/β and Ig H/L), full-length, V(D)J transcript sequencing from the same, individual cells will be performed on frozen PBMCs isolated from a total of 40 patients. Briefly, frozen PMBCs will be thawed and dissociated to obtain single cell suspensions and red blood cell lysis will be performed on the single cell suspensions. Sequencing libraries will be prepared for each sample as per the Chromium Single Cell V(D)J Reagent Kits and instructions. Approximately up to ~10,000 cells per sample will be loaded onto the Chromium Controller. Barcoded cDNA will be generated, and following amplification, the cDNA will be split to generate three sequencing libraries: one for gene expression, one for enrichment of α/β TCRs, and one for enrichment of Ig sequences. Sequencing of both gene expression and V(D)J enriched libraries will be performed on Illumina HiSeq 4000 using paired-end sequencing, with a 150 bp (R1), 8 bp (i7) and 150 bp (R2) read configuration. Analysis of single cell gene expression sequencing data will be performed using Cell Ranger. Clustering will be performed using Cell Ranger and viewed in Loupe Cell Browser; Single cell TCR and Ig sequencing data will be analyzed using Cell Ranger and visualized using the Loupe V(D)J Browser. Cell Ranger output files will be utilized for tertiary data analysis by single cell RNA sequencing data analysis programs such as Seurat and Monocle 2. TCR/BCR sequencing data will be intersected with gene expression profiles to ascertain both the functional phenotype of the individual immune cells and the clonality of these cells to examine the clonal expansion. This high dimensional dataset can provide invaluable insight in to the functional immune cell signatures that could be predictive of irAEs. The inventors have carried out our pilot experiments using the Illumina® Bio-Rad Single-Cell Sequencing Solution using ddseq-Biorad instrument to demonstrate the high-quality sc-RNA-Seq data achieved with fresh and frozen PBMCs isolated from same healthy human donor (FIGS. 14A-D and unpublished). Data was analyzed using R package and Seurat software package. There was no statistical difference in gene expression between the samples or within each subpopulation between the fresh and frozen samples. These data demonstrate the feasibility of using frozen PBMCs to assess the immune system in cancer immunotherapy patients in our current proposal utilizing 10× chromium technologies. ScRNA-seq using 10× chromium technologies reveal changes in subsets of immune cell populations after immunotherapy administration (FIGS. 15A-B).

Example 5—Clinical Example

Because irAE may occur at any point throughout checkpoint inhibitor therapy, the inventors evaluated in clinical and biomarker detail a case of a patient with advanced non-small cell lung cancer (NSCLC) treated with combined anti-CTLA4 and anti-PD1 checkpoint blockade. The patient developed clinically distinct and metachronous irAEs over a period of more than 18 months. Serial assessment of autoantibodies and cytokine levels provides insight into dynamic changes in cellular and humoral immunity underlying these events.

Peripheral blood samples were collected from the patient at pre-treatment baseline and multiple post-treatment initiation time-points, including at toxicity onset (FIG. 16A). At each time point, 4 tubes with a total of approximately 25.5 ml blood were collected. Blood samples were centrifuged at 3000 rpm at 4° C. for 15 min to obtain plasma and stored in aliquots at −80° C.

FIG. 16A provides an overview of the clinical course. A 53-year-old woman with a history of endometriosis, migraine headaches, and 35 pack-years smoking developed progressive mid-back pain. Spine magnetic resonance imaging (MRI) demonstrated a paraspinous soft tissue mass at T12-L1, as well as pulmonary nodules. Chest computed tomography (CT) confirmed multiple bilateral pulmonary nodules, with a dominant right lower lobe 1.7 cm tumor. Percutaneous core needle biopsy revealed adenocarcinoma consistent with lung primary, with a KRAS G12C mutation. The patient initiated treatment with a combination ipilimumab 1 mg/kg IV every 6 weeks and nivolumab 3 mg/kg IV every 2 weeks.

After almost 4 months of treatment, the patient developed an erythematous rash on the left arm and both legs, which was considered a grade 1 dermatologic irAE. After five days of prednisone 10 mg daily, the rash resolved. However, shortly thereafter the rash recurred and involved both feet. She received a second course of prednisone 10 mg daily for 5 days, with resolution of her symptoms.

After almost 5 months of therapy, the patient presented with weakness, fatigue, and had orthostatic vital sign changes. Laboratory assessment revealed low serum concentrations of adrenocorticotropic hormone (ACTH) (<5 pg/mL) and cortisol (0.8μ/dL). The clinical and laboratory findings were suggestive of hypophysitis (hypopituitarism). After initiation of replacement steroids with hydrocortisone 10 mg twice daily, her symptoms rapidly improved. After ~12 months of therapy, the patient developed a persistent upper respiratory infection that was treated with both antibiotics (amoxicillin/clavulanic acid) and steroids (prednisone 40 mg daily for five days).

Approximately 18 months after treatment initiation, she developed Grade 2 blepharitis (eyelid swelling, no image available) considered likely related to checkpoint inhibitor therapy. Immunotherapy was interrupted, and the patient received another 5-day course of prednisone 40 mg daily. At ~18.5 months after treatment initiation, the patient developed herpes zoster in a flank/abdominal distribution, for which she received acyclovir. Immunotherapy was restarted after completion of antiviral therapy.

At 21.5 months, the patient first noted an abnormal cold sensation in her fingers and toes, with symptomatic progression to painful, swollen digits that turned white upon cold exposure and then red upon rewarming (FIG. 16B). Following diagnostic guidelines, she was diagnosed with Grade 1 Raynaud's phenomenon. While treatment with calcium channel blockers led to symptomatic improvement initially, she subsequently required hydroxychloroquine therapy.

Regarding efficacy, the patient achieved a deep partial (near complete) radiographic response, which was sustained more than 29 months after treatment initiation at the time of this report. At approximately 4 months, a small number of apparently new liver lesions emerged, which regressed on subsequent imaging and were considered possible pseudoprogression.

Monitoring of cytokine and chemokine levels was performed using Bio-Plex Pro Human Chemokine 40-plex Panel (Bio-Rad Laboratories, Hercules, California) according to the manufacturer's instructions using a Luminex 200 System. The list of cytokines and chemokines are provided in Supplemental Table 1. Bio-Plex Manager™ 6.1 software was used for data analysis. Cytokine and chemokine concentrations (pg/mL) were determined on the basis of the fit of a standard curve for mean fluorescence intensity versus pg/mL. Cytokine analysis is representative of two independent experimental repeats. Error bars represent means±standard deviation.

Hierarchical clustering of the 40 cytokines and chemokines demonstrated dynamic changes in the serum levels (FIG. 17A). Thirty cytokines were upregulated two-fold or more at 11 weeks after the initiation of immunotherapy. At the 4-month time-point, coinciding with the development of hypophysitis, 12 cytokines were upregulated greater than two-fold compared to baseline. At this time-point, increases in serum levels of CXCL9, CXCL10, CCL2, CXCL13 and MIF were considerably greater than those noted at the 11-week time-point. Notably, MIF (which has been associated with hypophysitis) demonstrated the greatest elevation (FIG. 17B). At 9 months, most cytokines were reduced to baseline levels, with the exception of CXCL9, CXCL10, CXCL11 and IL16. At month 11, coincident with the onset of the patient's upper respiratory infection, the inventors observed a major spike in serum levels of 30 cytokines, which returned to prior levels by month 13. With the exception of CXCL9 and CXCL10—which remained upregulated greater than two-fold throughout the entire course of treatment—cytokine/chemokine levels were stable from month 13 month onward, including at the time of Raynaud's phenomenon.

Autoantibody reactivates against a panel of 124 autoantigens were measured using an autoantigen microarray platform developed by Microarray core of UTSW (microarray-.swmed.edu/products/category/protein-array/). Briefly, 2 μL of serum was pre-treated with DNAse-I and then diluted 1:50 in PBST buffer for autoantibody profiling. The autoantigen array bearing 124 autoantigens and 4 control proteins were printed in duplicates onto Nitrocellulose film slides (Grace Bio-Labs). The diluted serum samples were incubated with the autoantigen arrays, and autoantibodies were detected with cy3-conjugated anti-mouse IgG and cy5-conjugated anti-mouse IgM (1:2000, Jackson ImmunoResearch Laboratories), using a Genepix 4200A scanner (Molecular Device) with laser wavelength of 532 nm and 635 nm. The resulting images were analysed using Genepix Pro 7.0 software (Molecular Devices). The median of the signal intensity for each spot was calculated and subtracted from the local background around the spot, and the average value was calculated from duplicate spots. The background subtracted signal intensity of each antigen was normalized to the average intensity of the mouse IgG and IgM which were spotted on the array as internal controls. Finally, the net fluorescence intensity (NFI) for each antigen was calculated by subtracting a PBS control which was included for each experiment as negative control. Signal-to-noise ratio (SNR) was used as a quantitative measurement of the true signal above background noise. SNR values equal to or greater than 3 were considered significantly higher than background. The NFI of each autoantibody was used to generate heatmaps using Cluster and Treeview software (bonsai.hgc.jp/~mdehoon/software/cluster/software.htm).

Hierarchical clustering of 124 autoantibodies demonstrated dynamic changes in serum levels of multiple autoantibodies during immunotherapy regimen in the patient (FIG. 18A). In contrast to cytokine levels, there were no meaningful changes in antibody levels until month 9. At that point, with no clinical correlate, the inventors observed a greater than two-fold increase in levels of 46 autoantibodies compared to baseline, with subsequent reduction to near baseline levels until month 19. At month 19, coincident with blepharitis and weeks before the emergence of Raynaud's phenomenon, the inventors observed a rise in multiple autoantibody levels (FIG. 18B). In particular, levels of anti-phospholipid antibodies (including anti-beta-2 glycoprotein), anti-dsDNA, anti-AGTR-1, anti-vitronectin and anti-prothrombin antibodies—which have known associations with Raynaud's disease—were upregulated compared to baseline.

Autoantibody reactivates against a panel of 124 autoantigens were measured using an autoantigen microarray platform developed by Microarray core of UTSW (microarray-.swmed.edu/products/category/protein-array/). Briefly, 2 μL of serum was pre-treated with DNAse-I and then diluted 1:50 in PBST buffer for autoantibody profiling. The autoantigen array bearing 124 autoantigens and 4 control proteins were printed in duplicates onto Nitrocellulose film slides (Grace Bio-Labs). The diluted serum samples were incubated with the autoantigen arrays, and autoantibodies were detected with cy3-conjugated anti-mouse IgG and cy5-conjugated anti-mouse IgM (1:2000, Jackson ImmunoResearch Laboratories), using a Genepix 4200A scanner (Molecular Device) with laser wavelength of 532 nm and 635 nm. The resulting images were analysed using Genepix Pro 7.0 software (Molecular Devices). The median of the signal intensity for each spot was calculated and subtracted from the local background around the spot, and the average value was calculated from duplicate spots. The background subtracted signal intensity of each antigen was normalized to the average intensity of the mouse IgG and IgM which were spotted on the array as internal controls. Finally, the net fluorescence intensity (NFI) for each antigen was calculated by subtracting a PBS control which was included for each experiment as negative control. Signal-to-noise ratio (SNR) was used as a quantitative measurement of the true signal above background noise. SNR values equal to or greater than 3 were considered significantly higher than background. The NFI of each autoantibody was used to generate heatmaps using Cluster and Treeview software.

The inventors also performed extensive biomarker analysis on a patient with lung cancer who developed autoimmune type 1 diabetes mellitus after initiation of treatment with anti-PD1 therapy. Hierarchical clustering of the 40 cytokines and chemokines was performed. Eleven cytokines were upregulated two-fold or more at 6 weeks after the initiation of immunotherapy compared to baseline as demonstrated in the heatmap (FIG. 19A) coinciding with the development of Type I diabetes. Notably, IL-1β, a proinflammatory cytokine produced by activated macrophages that plays a key role in mediating inflammation and R cell destruction was upregulated at the time of development of immune-related adverse event. Hierarchical clustering of 124 autoantibodies demonstrated dynamic changes in serum levels of multiple autoantibodies during immunotherapy regimen in the patient. The inventors observed a greater than 1.5-fold increase in levels of 58 autoantibodies compared to baseline at 6-week post immunotherapy. In particular, levels of anti-glutamate decarboxylase-65/GAD-2 antibodies—that has known associations with Type-I diabetes was upregulated compared to baseline (FIG. 19B).

All of the compositions and methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

VI. REFERENCES

The following references, to the extent that they provide exemplary procedural or other details supplementary to those set forth herein, are specifically incorporated herein by reference.

"*Antibodies: A Laboratory Manual*," Cold Spring Harbor Press, Cold Spring Harbor, NY, 1988.
Abbondanzo et al., *Am. J. Pediatr. Hematol. Oncol.,* 12(4), 480-489, 1990.
Abiola et al., *Nat Rev Genet* 4:911-6, 2003.
Allison et al., *Eur J Immunol* 28:949-60, 1998a.
Allison et al., *Novartis Found Symp* 215:92-8; discussion 98-102, 186-90, 1998b
Allred et al., *Arch. Surg.,* 125(1), 107-113, 1990.
Ansell et al., *N Engl J Med* 372:311-9, 2015.
Blogowski et al., *PLoS One* 9:e97613, 2014.
Brown et al., *J. Immunol. Meth.,* 12; 130(1), :111-121, 1990.
Campbell, *In: Monoclonal Antibody Technology, Laboratory Techniques in Biochemistry and Molecular Biology*, Vol. 13, Burden and Von Knippenberg, Eds. pp. 75-83, Amsterdam, Elsevier, 1984.
Cooper et al., *J Autoimmun* 33:197-207, 2009.
De Jager et al., *Semin. Nucl. Med.* 23(2), 165-179, 1993.
Doolittle and Ben-Zeev, *Methods Mol. Biol.,* 109, 215-237, 1999.
Early Breast Cancer Trialists' Collaborative Group, *Lancet* 351:1451-67, 1998.
Gianchecchi et al., *Autoimmun Rev* 12:1091-100, 2013.
Gubin et al., *Nature* 515:577-81, 2014.
Gulbis and Galand, *Hum. Pathol.* 24(12), 1271-1285, 1993.
Hamanishi et al., *J Clin Oncol* 33; 4015-22, 2015.
Horvat et al., *J Clin Oncol* 33:3193-8, 2015.
Horvat et al., *J Clin Oncol* 33:3193-8, 2015.
Howell et al., *Lung Cancer* 88:117-23, 2015.
Kantola et al., *Br J Cancer* 107:1729-36, 2012.
Khan et al., *JAMA Oncol* 2:1507-1508, 2016.
Khan et al., *JAMA Oncol,* 2016 Jun. 4. Epub ahead of print.
Khan et al., *JAMA Oncology* 2:1507-8, 2016.
Khan et al., *Lung Cancer* 115:97-102, 2018.
Kristiansen et al., *Genes Immun* 1:170-84, 2000.
Le et al., *N Engl J Med* 372:2509-20, 2015.
Li and Wakeland, *Genomics Proteomics Bioinformatics* 13:205-7, 2015.
Li et al., *Arthritis Res Ther* 13:R38, 2011.
Li et al., *Arthritis Res Ther* 13:R38, 2011.
Li et al., *Clin Exp Immunol* 147:60-70, 2007.
Li et al., *Clin Exp Immunol* 159:281-91, 2010.
Marshall et al., *PLoS One* 12:e0172821, 2017.
McDermott et al., *J Clin Oncol* 33:2013-20, 2015.
Nakamura et al., In: *Enzyme Immunoassays: Heterogeneous and Homogeneous Systems*, Chapter 27, 1987.
Olsen and Karp, *Nat Rev Rheumatol* 10:181-6, 2014.
Osorio et al., *Ann Oncol* 28:583-589, 2017.
Postow et al., *N Engl J Med* 372:2006-17, 2015.
Postow et al., *N Engl J Med* 372:2006-17, 2015.
Raj et al., *Elife* 5, 2016.
Remington's Pharmaceutical Sciences, 15th Ed., 3:624-652, 1990.
Romo-Tena et al., *Autoimmun Rev* 12:1171-6, 2013.
Rotondi et al. *Endocr Rev* 28:492-520, 2007.
Tan et al., *Arthritis Rheum* 40:1601-11, 1997.
Tan et al., *Arthritis Rheum* 40:1601-11, 1997.
Tarhini et al., *J Immunother Cancer* 3:39, 2015.
Topalian et al., *N Engl J Med* 366:2443-54, 2012.
U.S. Pat. No. 3,817,837
U.S. Pat. No. 3,850,752
U.S. Pat. No. 3,939,350
U.S. Pat. No. 3,996,345
U.S. Pat. No. 4,275,149
U.S. Pat. No. 4,277,437
U.S. Pat. No. 4,366,241
Wandstrat et al., *J Autoimmun* 27:153-60, 2006.
Wandstrat et al., *J Autoimmun* 27:153-60, 2006.
Wild, D. (ed.). "The Immunoassay Handbook," Waltham, MA, Elsevier; Chapter 9.15, 2013.
Wolchok et al., *N Engl J Med* 369:122-33, 2013.
Yamazaki et al., *Cancer Sci* 108:1022-1031, 2017.
Zandman-Goddard and Shoenfeld, *Autoimmun Rev* 1:329-37, 2002.

What is claimed is:

1. A method of treating a human subject to mitigate or prevent immunotherapy toxicity, the method comprising:

(a) providing a chemokine- and/or cytokine-containing sample from the subject prior to treatment with an immunotherapy;

(b) assessing chemokine and/or cytokine levels in the sample provided prior to treatment wherein the chemokines and/or cytokines comprise IL-8/CXCL8, MIG/CXCL9, and IP-10/CXCL10;

(c) administering a treatment to the subject, wherein the treatment comprises:

(i) an immunotherapy comprising one or more of an immune checkpoint inhibitor, a chimeric antigen receptor, an immunotoxin, an anti-CTLA4 antibody, an anti-PD1 antibody, or an anti-PD1 ligand (PD-L1) antibody when the chemokine and/or cytokine levels in the sample provided prior to treatment are at or above the populational average;

(ii) a non-immunotherapy treatment comprising one or more of a chemotherapy, a chemoembolization, a radiotherapy, a radiofrequency ablation, a hormone therapy, a bland b embolization, or a surgery, when the chemokine and/or cytokine levels in the sample provided prior to treatment are below the populational average; or (iii) an immunotherapeutic toxicity mitigating therapy comprising one or more of a corticosteroid, a TNF inhibitor, or a hormone replacement therapy, or reducing one or more doses of an immunotherapy selected from one or more of an immune checkpoint inhibitor, a chimeric antigen receptor, or an immunotoxin, when the chemokine and/or cytokine levels in the sample provided prior to treatment are below the populational average.

2. The method of claim 1, wherein the sample is a whole blood, serum, plasma, or other body fluid.

3. The method of claim 1, wherein the immunotherapy toxicity is cancer immunotherapy toxicity.

4. The method of claim 1, further comprising:

assessing the level of an autoantibody in the same or a different sample obtained from the subject.

5. The method of claim 4, wherein the autoantibody level is assessed using a plurality of antigens selected from: Cardolipin, DGPS, Heparan HSPG, Nup62, SP100, CENP-A, dsDNA, Heparin, PCNA, Sphingomyelin, CENP-B, EBNA1, Heperan Sulfate, Peroxiredoxin 1, SRP54, Chondroitin Sulfate C, Elastin, Histone-total, Phophatidylinositol, ssDNA, Chromatin, Entactin EDTA, human genomic DNA, PL-12, ssRNA, Collagen I, Factor I, Intrinsic Factor, PL-7, T1F1 GAMMA, Collagen II, Factor P, 10-1, PM/Scl-100, Thyroglobulin, Collagen III, FactorB, KU (P70/P80), PM/Scl-75, TNFa, Collagen IV, FactorD, La/SSB, POLB, Topoisomerase I, Collagen V, FactorH, Laminin, PR3, TPO, Collagen VI, Fibrinogen IV, LC1, Proteoglycan, TTG, complement C1q, Fibrinogen S, LKM1 Prothrombin protein, U1-snRNP-68, complement C3, Fibronectin, M2 Antigen, Ribo phospho protein P1, U1-snRNP-A, complement C3a, GSM (disso), Matrigel, Ribo phospho protein P2, U1-snRNP-BB', complement C3b, Gliadin (IgG), MDAS, Ribo phosphoprotein P0, U1-snRNP-C, complement C4, Glycated Albumin, Mi-2, Ro/SSA (52 KDa), Vimentin, anti-Ig, IgG Control, β2-microglobulin, β2-glycoprotein I, and/or Vitronectin.

6. The method of claim 4, wherein the autoantibody level is assessed using a plurality of antigens selected from: CMV-G, Beef_Bos taurus, ubiquitin-like modifier activating anzyme 2 (UBA2), CMV-M, Shrimp_Penacidae, NY-ESO-1, CMV EXT-2, Peanut_*Arachis hypogaea*, Prostatic Acid Phosphatase, CMV GRADE III, Wheat (Whole_*Triticum aestivum*), Prostate Specific Membrane Antigen, HEPATITIS A, Mite, House Dust_*Blomia tropicalis*, MAGEA3, HAV CONCENTRATE, Bermuda_*Cynodon dactylon*, FOLH1, HSV-1, Cedar, Red_*Juniper rus virginiana*, PSA, HSV-2, Plantain (English_*Plantago lanceolata*), CA 125, RUBEOLA, Honey Bee_*Apis mellifera*, CEA, RSV, 3-hydroxy-3-methylglutaryl-coenzyme A reductase, PSMA/FOLH1/NAALADase 1, ROTAVIRUS SA-11, Aminoacyl-tRNA Synthetase, Myosin Light Chain, RUBELLA VIRUS GRADE III, Asparaginyl-tRNA Synthetase(KS), Muscarinic receptor, RUBELLA VIRUS GRADE IV, Glycyl-tRNA Synthetase(EJ), Albumin Bovine fraction V, RUBELLA GRACE IV, Lysyl-tRNA Synthetase, AQP4, RSVP, Phenylalanyl-tRNA Synthetase 2, DNA Polymerase beta Protein, TOXOPLASMA Antigen, Human Cytosolic 5'-nucleotidase 1A, EBV EBNA1, VZV, glutaminyl-tRNA Synthetase, AGTR1 (angiotension receptor1), VZV GRACE II, MORC family CW-type zinc ringer 3 (MORC3), Collagenase A, HUMAN AZUROCDIN, signal recognition particle 14 kDa, Collagenase D, House Dust, SUMO1 activating enzyme subunit 1 (SAE1), Tetanus toxin, Dog Dander, tryptophanyl-tRNA Synthetase(WARS), Ig Control, Dog Epithelia, tyrosyl-tRNA Synthetase(YARS), and/or Anti-Ig.

7. The method of claim 4, wherein the autoantibody level is assessed using a plurality of antigens selected from: Cardolipin, DGPS, Heparan HSPG, Nup62, SP100, CENP-A, dsDNA, Heparin, PCNA, Sphingomyelin, CENP-B, EBNA1, Heperan Sulfate, Peroxiredoxin 1, SRP54, Chondroitin Sulfate C, Elastin, Histone-total, Phophatidylinositol, ssDNA, Chromatin, Entactin EDTA, human genomic DNA, PL-12, ssRNA, Collagen I, Factor I, Intrinsic Factor, PL-7, T1F1 GAMMA, Collagen II, Factor P, 10-1, PM/Scl-100, Thyroglobulin, Collagen III, FactorB, KU (P70/P80), PM/Scl-75, TNFa, Collagen IV, FactorD, La/SSB, POLB, Topoisomerase I, Collagen V, FactorH, Laminin, PR3, TPO, Collagen VI, Fibrinogen IV, LC1, Proteoglycan, TTG, complement C1q, Fibrinogen S, LKM1Prothrombin protein, U1-snRNP-68, complement C3, Fibronectin, M2 Antigen, Ribo phospho protein P1, U1-snRNP-A, complement C3a, GSM (disso), Matrigel, Ribo phospho protein P2, U1-snRNP-BB', complement C3b, Gliadin (IgG), MDAS, Ribo phosphoprotein P0, U1-snRNP-C, complement C4, Glycated Albumin, Mi-2, Ro/SSA (52 KDa), Vimentin, anti-Ig, IgG Control, P2-microglobulin, P2-glycoprotein I, Vitronectin, CMV-G, Beef_Bos taurus, ubiquitin-like modifier activating anzyme 2 (UBA2), CMV-M, Shrimp_Penacidae, NY-ESO-1, CMV EXT-2, Peanut_*Arachis hypogaea*, Prostatic Acid Phosphatase, CMV GRADE III, Wheat (Whole_*Triticum aestivum*), Prostate Specific Membrane Antigen, HEPATITIS A, Mite, House Dust_*Blomia tropicalis*, MAGEA3, HAV CONCENTRATE, Bermuda_*Cynodon dactylon*, FOLH1, HSV-1, Cedar, Red_*Juniper rus virginiana*, PSA, HSV-2, Plantain (English_*Plantago lanceolata*), CA 125, RUBEOLA, Honey Bee_*Apis mellifera*, CEA, RSV, 3-hydroxy-3-methylglutaryl-coenzyme A reductase, PSMA/FOLH1/NAALADase 1, ROTAVIRUS SA-11, Aminoacyl-tRNA Synthetase, Myosin Light Chain, RUBELLA VIRUS GRADE III, Asparaginyl-tRNA Synthetase(KS), Muscarinic receptor, RUBELLA VIRUS GRADE IV, Glycyl-tRNA Synthetase(EJ), Albumin Bovine fraction V, RUBELLA GRACE IV, Lysyl-tRNA Synthetase, AQP4, RSVP, Phenylalanyl-tRNA Synthetase 2, DNA Polymerase beta Protein, TOXOPLASMA Antigen, Human Cytosolic 5'-nucleotidase 1A, EBV EBNA1, VZV, glutaminyl-tRNA Synthetase, AGTR1 (angiotension receptor1), VZV GRACE II, MORC family CW-type zinc ringer 3 (MORC3), Collagenase A, HUMAN AZUROCDIN, signal recognition particle 14 kDa, Collagenase D, House Dust, SUMO1 activating enzyme subunit 1 (SAE1), Tetanus toxin, Dog Dander, tryptophanyl-tRNA Synthetase(WARS), Ig Control, Dog Epithelia, tyrosyl-tRNA Synthetase(YARS), and/or Anti-Ig.

8. The method of claim 1, wherein the assessing of step (b) comprises measuring the chemokines and/or cytokines with one or more of ELISA, RIA, Western blot, microarray, bead array, cartridges, lateral flow, or line-probe assays.

9. The method of claim 1, further comprising:

repeating steps (a)-(b) at a second time point, thereby permitting assessment of a change in immunotherapeutic toxicity risk.

10. The method of claim 1, wherein the subject has previously been diagnosed with an autoimmune disease.

11. The method of claim 1, wherein the subject has not previously been diagnosed with an autoimmune disease.

12. The method of claim 1, further comprising:

classifying immunotherapy toxicity based on organ or organ system in the subject.

13. The method of claim 1, wherein the subject is further characterized as receiving a molecular targeted therapy, a chemotherapy, a chemoembolization, a radiotherapy, a radiofrequency ablation, a hormone therapy, a bland embolization, a surgery, or a second distinct immunotherapy.

14. The method of claim 1, wherein the cytokines and/or chemokines are further selected from: CCL19, CCL23, CXCL11, CXCL16, and MIF35.

15. The method of claim 4, wherein the autoantibody level is assessed using antigens Entactin EDTA and Fibrinogen S.

* * * * *